United States Patent [19]
Santerre et al.

[11] Patent Number: 4,727,028
[45] Date of Patent: Feb. 23, 1988

[54] RECOMBINANT DNA CLONING VECTORS AND THE EUKARYOTIC AND PROKARYOTIC TRANSFORMANTS THEREOF

[75] Inventors: Robert F. Santerre, Zionsville; Ramachandra N. Rao, Indianapolis, both of Ind.

[73] Assignee: Eli Lilly and Company, Indianapolis, Ind.

[21] Appl. No.: 538,051

[22] Filed: Sep. 30, 1983

Related U.S. Application Data

[63] Continuation-in-part of Ser. No. 487,787, Apr. 22, 1983, abandoned, which is a continuation-in-part of Ser. No. 362,215, Mar. 26, 1982, abandoned, which is a continuation-in-part of Ser. No. 276,445, Jun. 22, 1981, abandoned.

[51] Int. Cl.$^4$ .................. C12N 5/00; C12N 15/00; C12N 9/12; C12N 1/00; C12N 1/20; C12N 1/14; C12N 1/16; C12P 21/00; C12P 19/34; C07H 21/04

[52] U.S. Cl. .................. 435/240.2; 435/68; 435/91; 435/172.1; 435/172.3; 435/194; 435/243; 435/253; 435/254; 435/255; 435/317.1; 435/320; 536/27; 935/11; 935/14; 935/29; 935/34; 935/70; 935/71; 935/72; 935/73; 935/68; 935/84

[58] Field of Search .................. 435/68, 70, 71, 91, 435/172.3, 253, 240, 241, 849, 317, 172.1, 317.1, 240.2, 194, 320; 536/27; 935/11, 14, 29, 34, 70, 71, 72, 73, 68, 84

[56] References Cited

U.S. PATENT DOCUMENTS 4,419,446 12/1983 Howley et al. .................. 435/317

FOREIGN PATENT DOCUMENTS 0068740 5/1983 European Pat. Off. ......... 435/172.3

OTHER PUBLICATIONS

Lewin, "Gene Expression", vol. 1, John Wiley & Sons, New York, 1974, pp. 425–436.

Gritz and Davies, Gene 25 (1983), 179–188.
Guarente and Ptashne, Proc. Natl. Acad. Aci. USA, 1981, vol. 78(4), 2199–2203.
Sherman et al., Cell, 1980, vol. 20, 215–222.
Smith et al., Cell, 1979, vol. 16, 753–761.

(List continued or next page.)

*Primary Examiner*—James Martinell
*Attorney, Agent, or Firm*—Gerald V. Dahling; Leroy Whitaker

[57] ABSTRACT

The present invention comprises novel recombinant DNA cloning and expression vectors which confer hygromycin B and/or G418 resistance to eukaryotic and prokaryotic host cells. The novel recombinant DNA vectors are derived from plasmid pKC203, a plasmid which can be isolated from *E. coli* JR225 (ATCC 31912). The hygromycin B and G418 resistance-conferring genes can be isolated on the 7.5 kb BglII restriction fragment or the 2.5 kb SalI-BglII restriction fragment of plasmid pKC203. The eukaryotic recombinant DNA vectors of the present invention are prepared by inserting such resistance-conferring restriction fragments into a vector, such as plasmid pSV5gpt, that comprises a eukaryotic promoter and the necessary functions for maintenance of the vector as an extrachromosomal element or as an integrated sequence in the host cell chromosomal DNA. Furthermore, the present invention comprises useful derivatives of plasmid pKC203 which, although comprising no eukaryotic elements, are useful recombinant vectors for *E. coli* and other prokaryotes and serve as starting material for the construction of eukaryotic vectors that confer hygromycin B and/or G418 resistance to eukaryotic host cells. One useful derivative of plasmid pKC203 is constructed by circularizing the ~7.5 kb BglII restriction fragment of plasmid pKC203 to form plasmid pSC701, which can be further digested with HaeII or Sau3AI to form smaller plasmids. The present invention also comprises the novel transformants of the aforementioned recombinant DNA vectors.

111 Claims, 10 Drawing Figures

OTHER PUBLICATIONS

Faye et al., Proc. Natl. Acad. Sci. USA, 1981, vol. 78(4), 2258–2262.
Montgomery et al., Cell, 1978, vol. 14, 673–680.
Jimenez and Davies, 1980, Nature, 287:869.
Garapin et al., 1981, J. Mol. Biol., 150:1–14.
Davies et al: Antimicrob. Agents & Chemother., 14: 69 (1978).
Sutcliffe et al: in Genetic Engineering, Chakrabarty (ed.), CRC Press, pp. 83–111.
Davies et al: Am. Journal Tropical Med. & Hygiene, 29: Suppl. 1089 (1980).
Botstein et al: Recomb. DNA Tech. Bull., 2, No. 2, 49 (1979).
Maxam et al: Proc. Natl. Acad. Sci. USA, 74: 560 (1977).
Gritz et al: Chem. Abstr., 100: 97426n (1984), of Gene, 25: 179 (1983).
Hamer et al: Nature, 281: 35 (1979).
Mulligan et al.: Science, 209: 1422 (1980).

Restriction Site and Functional Map of Plasmid pKC203

Restriction Site and Functional Map of Plasmid pSV5 gpt

PY Tag — Polyoma Sequence
— SV40 Sequence

Restriction Site and Functional Map of Plasmid pKC222

Figure 6
Restriction Site and Functional Map of Plasmids pSC701 and pKC257
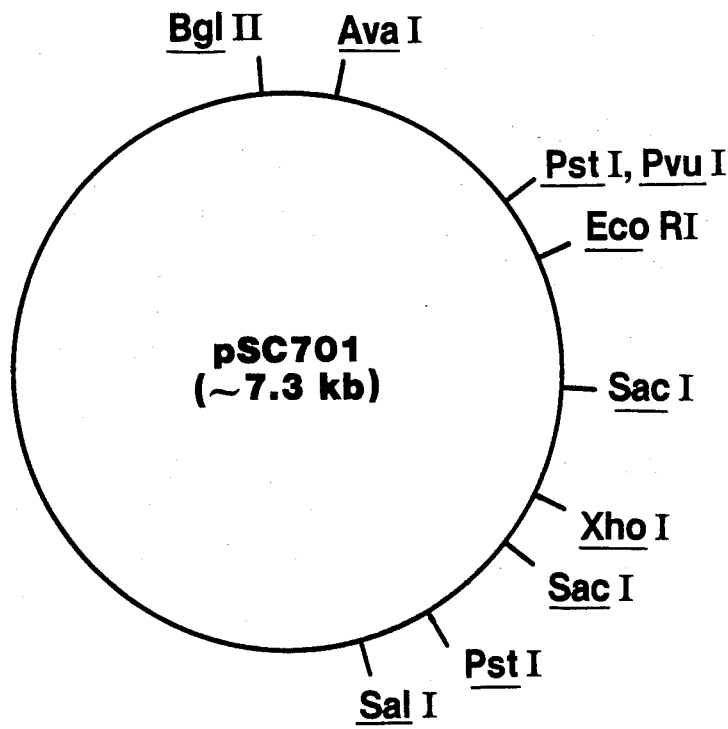
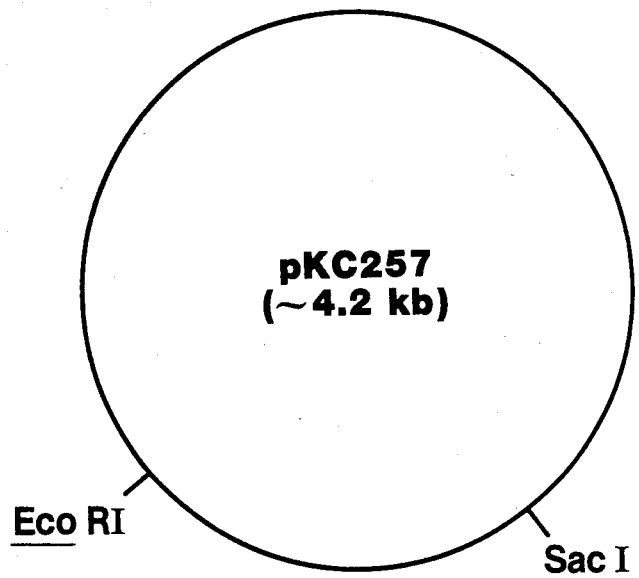

Figure 7
Restriction Site and Functional Map of Plasmids pKC259 and pKC261
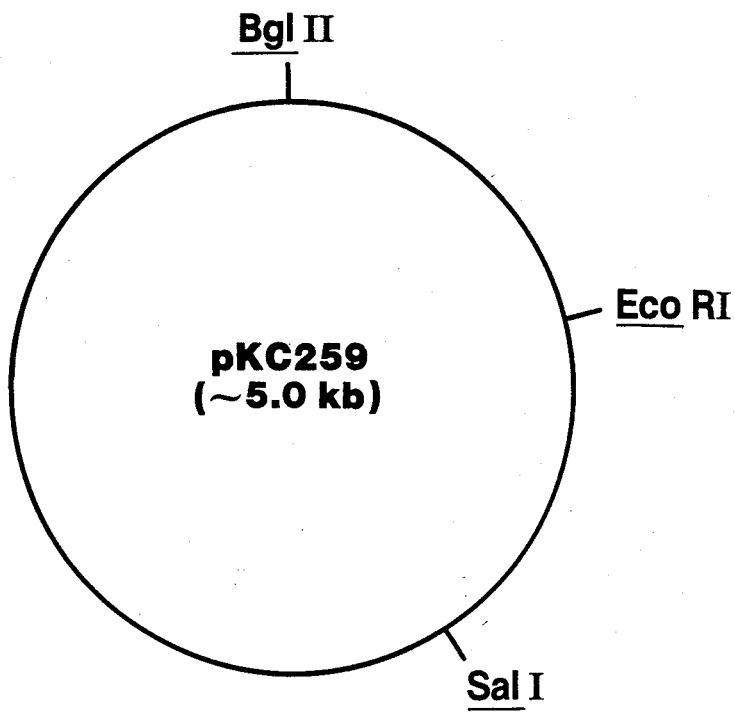
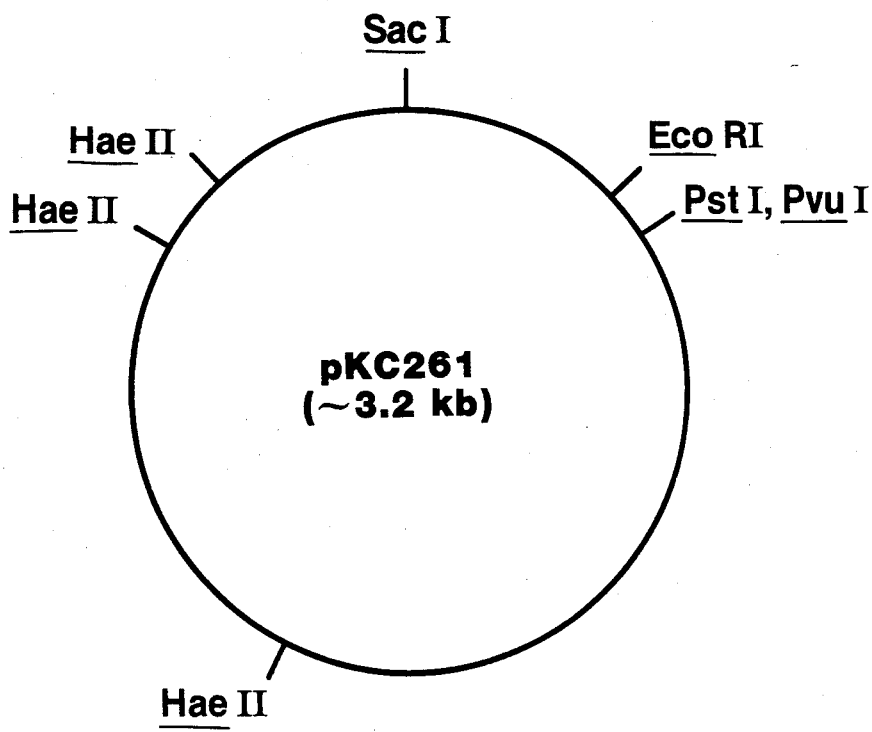

Figure 8
Restriction Site and Functional Map of Plasmids pKC275 and pKC264
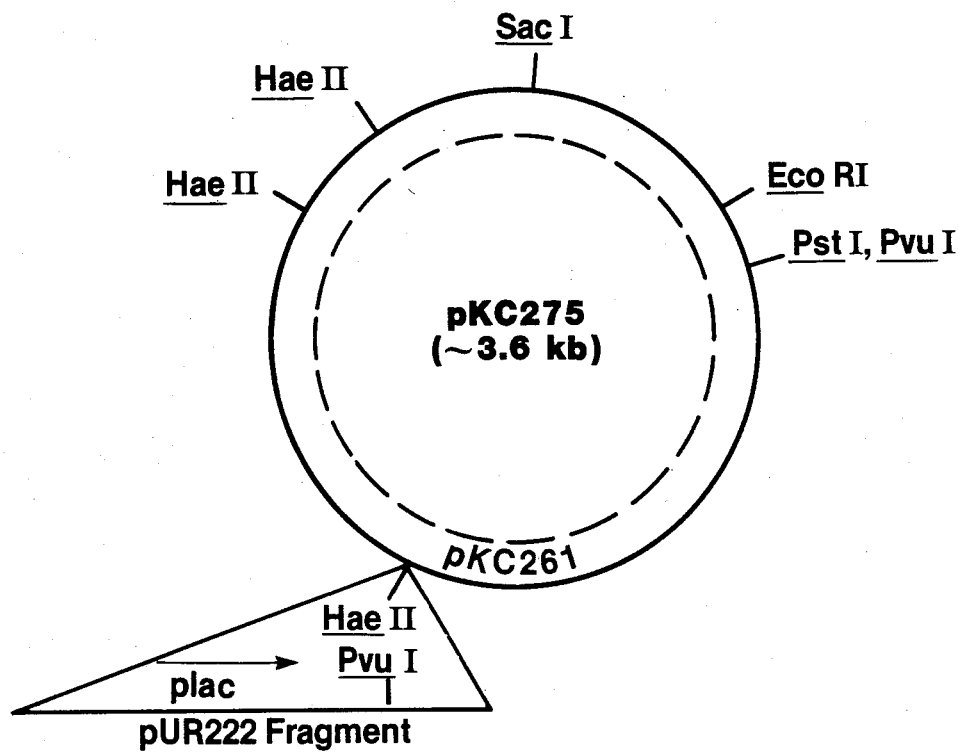
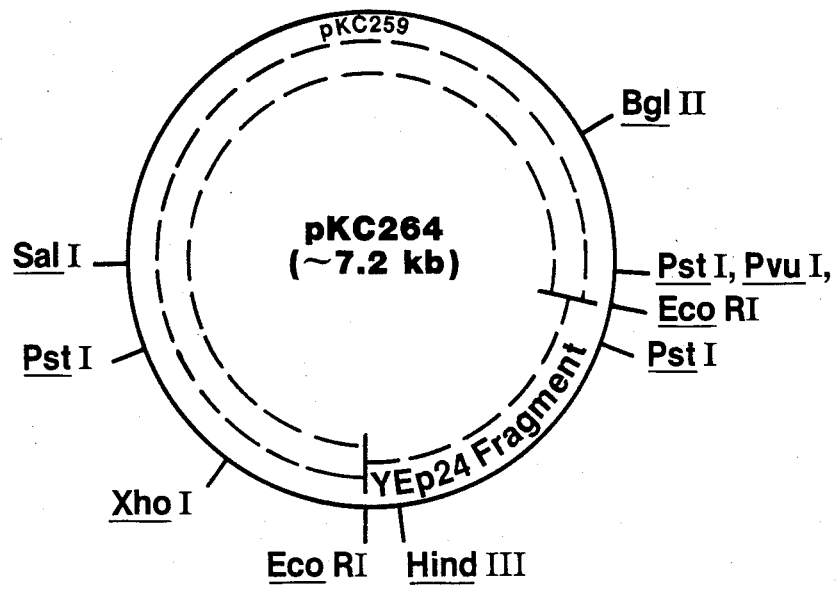

Restriction Site and Functional Map of Plasmids pLO314 — pLO321

1. pLO320 (~12.9 kb)
2. pLO318 (~12.5 kb)
3. pLO314 (~14.3 kb)
4. pLO316 (~13.5 kb)
5. pLO321 (~12.9 kb)
6. pLO319 (~12.5 kb)
7. pLO315 (~14.3 kb)
8. pLO317 (~13.5 kb)

Figure 10
Restriction Site and Functional Map of Plasmids pLO378 and pKC273
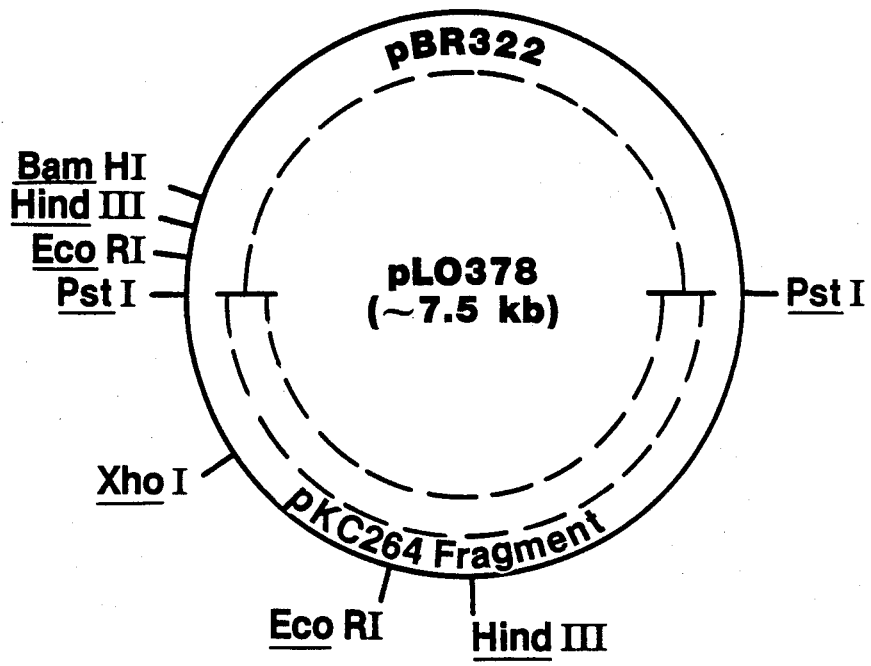
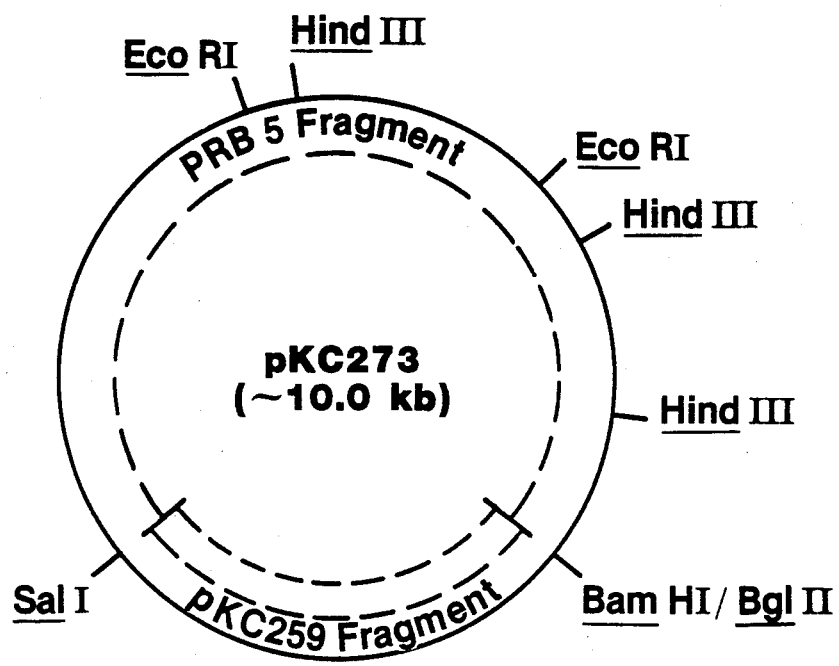

# 4,727,028

RECOMBINANT DNA CLONING VECTORS AND THE EUKARYOTIC AND PROKARYOTIC TRANSFORMANTS THEREOF

CROSS-REFERENCE

The present application is a continuation-in-part of copending application Ser. No. 487,787, filed Apr. 22, 1983, now abandoned, which is a continuation-in-part of application Ser. No. 362,215, filed Mar. 26, 1982, now abandoned, which is a continuation-in-part of application Ser. No. 276,445, filed June 22, 1981, now abandoned.

SUMMARY OF THE INVENTION

The present invention comprises novel recombinant DNA cloning vectors that convey hygromycin B and G418 (Daniels et al., 1973, Abstr. 137, 13th Interscience Conference On Antimicrobial Agents and Chemotherapy, Washington, D.C.) resistance to both eukaryotic and prokaryotic cells. The invention further provides transformants of the aforementioned vectors.

The present invention is particularly important because it solves the problem of how to identify, manipulate, and stabilize cloned DNA sequences that lack a selectable function in eukaryotic and prokaryotic cells. Heretofore, the development and exploitation of recombinant DNA technology in eukaryotic cells has been retarded and made difficult because of (1) the general lack of suitable cloning vectors that contain markers that are selectable in eukaryotic cells; (2) the inability to quickly amplify desired DNA sequences in eukaryotic cells; and (3) the slow generation time of eukaryotic cells in culture. These problems are now eliminated since the vectors of the present invention are functional and selectable in both eukaryotic and prokaryotic cells. Consequently, DNA sequences that are cloned onto the present versatile vectors can be conventionally manipulated and amplified in prokaryotic cells, thus avoiding the inconvenience and problems of doing the procedures in eukaryotic cells. Moreover, since the present vectors are both functional and selectable in eukaryotic cells, the vectors can be transformed following manipulation and amplification, directly into eukaryotic hosts without additional modification. This is not only advantageous but represents a significant advance in the technical art.

The ability to clone DNA into eukaryotic host cells and to readily select the transformants is important for the further and more sophisticated development of recombinant DNA technology. Since transformation, and consequently acquisition of plasmid DNA, is a very low frequency event, such a functional test is a practical necessity for determining which cell(s), of among the millions of cells, has acquired the plasmid DNA. This is important because DNA sequences that are non-selectable can be inserted onto the vectors to cause insertional inactivation of a particular antibiotic resistance gene. Therefore, upon transformation, cells containing the vector and the particular DNA sequence of interest can be isolated by appropriate antibiotic selection. The present vectors are particularly useful because they are highly versatile and can be transformed and selected in any hygromycin B or G418 sensitive eukaryotic or prokaryotic cell that can divide and take up DNA. This is important because to date, most progress in the recombinant DNA art has involved the production of eukaryotic polypeptides such as, for example, proinsulin, insulin A chain, insulin B chain, human growth hormone, bovine growth hormone, interferon, somatostatin, thymosin α1, and the like, in prokaryotic hosts. Prokaryotic cells are incapable of correctly attaching sugar moieties to eukaryotic polypeptides. Therefore, the production of post translationally modified eukaryotic polypeptides, such as the glycosylated polypeptides, by recombinant DNA techniques is not possible without a eukaryotic host and appropriate eukaryotic recombinant DNA cloning vectors.

The vectors of the present invention fill this need and broaden the scope and application of recombinant DNA technology. Consequently, the commercial production of both unmodified and posttranslationally modified proteins in eukaryotic cells is enhanced.

For purposes of the present invention as claimed herein, the following terms are as defined below.

Structural Gene—a DNA sequence that codes for a polypeptide.

Control Element—a DNA sequence that directs and regulates the transcription and expression of a structural gene.

Eukaryotic Promoter—a DNA sequence that in part promotes and regulates the expression of a structural gene in a eukaroytic cell.

Prokaryotic Replicon—a DNA sequence that controls and regulates the replication of DNA in a prokaryotic cell.

Recombinant DNA Cloning Vector—any agent, including but not limited to plasmids, bacteriophages, and viruses, consisting of a DNA molecule to which one or more additional DNA segments can or have been added.

Transformation—the introduction of DNA into a recipient host cell that changes the genotype and consequently results in a stable and heritable change in the recipient cell.

Insertional isomer—one of the two or more possible recombinant DNA molecules formed when a DNA fragment is inserted at one of two or more compatible sites on the recipient DNA.

BRIEF DESCRIPTION OF THE DRAWINGS

FIG. 6. The restriction site and functional map of plasmids pSC701 and pKC257.

FIG. 7. The restriction site and functional map of plasmids pKC259 and pKC261.

FIG. 8. The restriction site and functional map of plasmids pKC275 and pKC264.

FIG. 10. The restriction site and functional map of plasmids pLO378 and pKC273.

DETAILED DESCRIPTION OF THE INVENTION

The present invention comprises recombinant DNA cloning vectors comprising:
(a) eukaryotic promoter,
(b) one or two different structural genes and associated control elements that convey resistance to either or both antibiotics hygromycin B and G418 when transformed into a host cell that is sensitive to either or both antibiotics for which resistance is conveyed, said host cell being susceptible to transformation, cell division, and culture, and
(c) a prokaryotic replicon, said replicon being functional when said host cell is prokaryotic,
subject to the limitations that the one or two structural genes and associated control elements are adjacent to and, in a eukaryotic host cell, transcribed from the eukaryotic promoter, that a single gene and associated control element conveys resistance to either but not both hygromycin B and G418, and that the gene conveying resistance to G418 does not code for the enzyme phosphotransferase. In addition, the invention further comprises transformants containing the above described cloning vectors.

The present invention, as exemplified herein, exploits bacterial plasmid DNA that confers resistance to the aminoglycoside antibiotics hygromycin B and G418, for constructing novel plasmids that contain and express the resistance in hygromycin B or G418 sensitive eukaryotic and prokaryotic host cells. Thus, the present invention is useful for cloning DNA into virtually any type of cell. Furthermore, the ability of the vectors exemplified herein to confer resistance to antibiotics that are toxic in both eukaryotic and prokaryotic cells also provides a functional test for selecting and stabilizing cells that have acquired the vectors.

Figure 1:
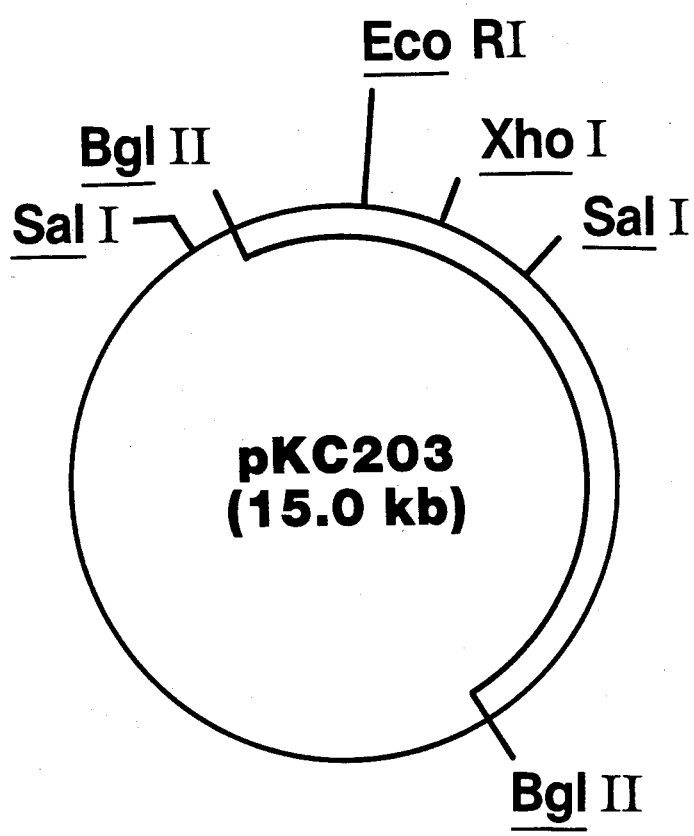
FIG. 1. The restriction site and functional map of plasmid pKC203.

The particular bacterial plasmid DNA sequence used in the present illustrative constructions, is the 7.5kb BglII restriction fragment, or derivatives thereof, of plasmid pKC203. Plasmid pKC203 is approximately 15kb in size and can be isolated readily from *E. coli* JR225 by conventional procedures. Strain *E. coli* JR225 is both known in the art (Davies and O'Connor, 1978, Antimicrobial Agents and Chemotherapy 14(1): 69), and also deposited and made part of the stock culture collection of the American Type Culture Collection, Rockville, Md., from which it is available to the public without restriction under the number ATCC 31912. A restriction and functional map of plasmid pKC203 is presented in FIG. 1 of the accompanying drawings. FIG. 1 and all subsequent figures are not drawn to scale.

Figure 2:
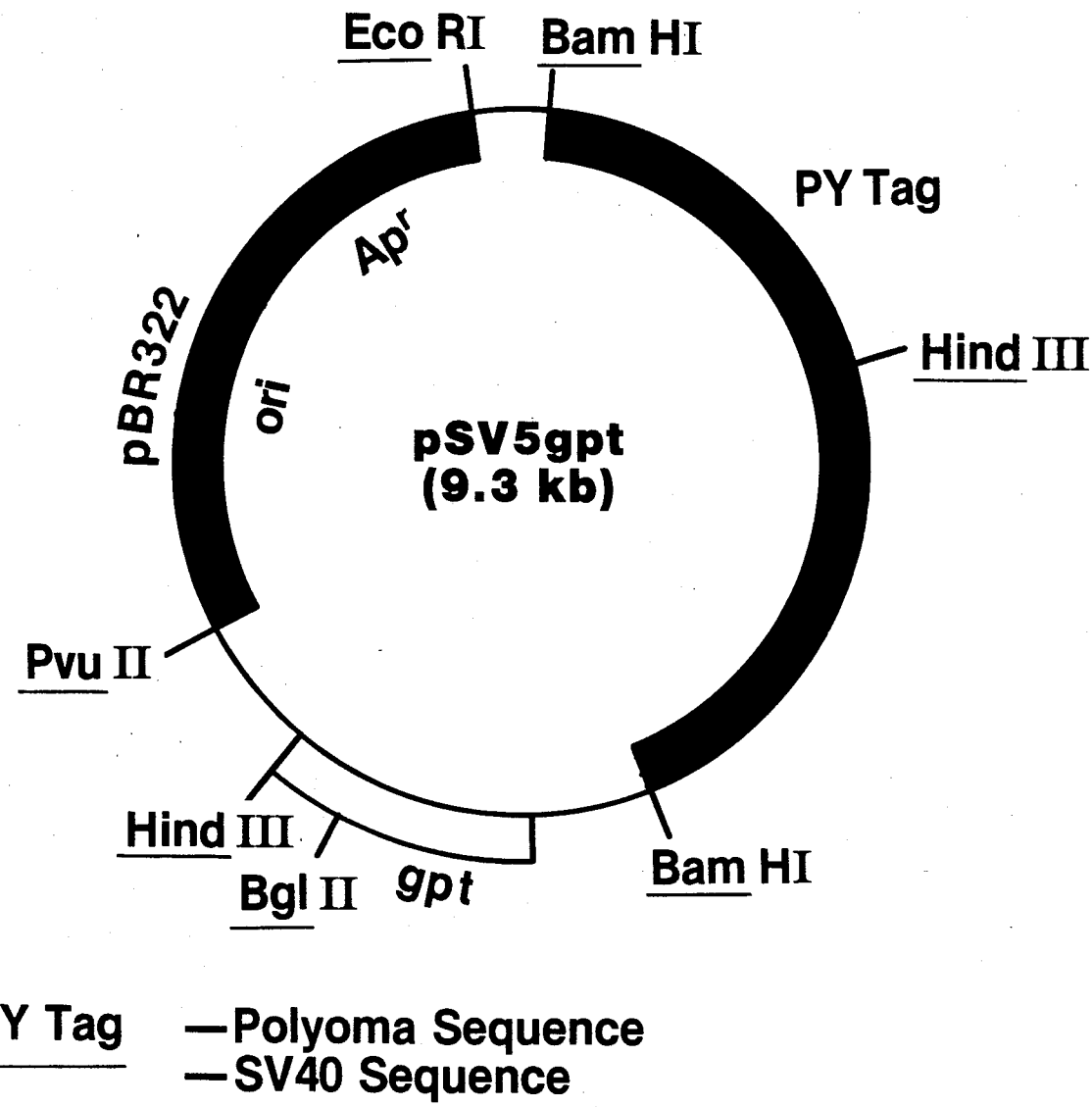
FIG. 2. The restriction site and functional map of plasmid pSV5gpt.
Figure 3:
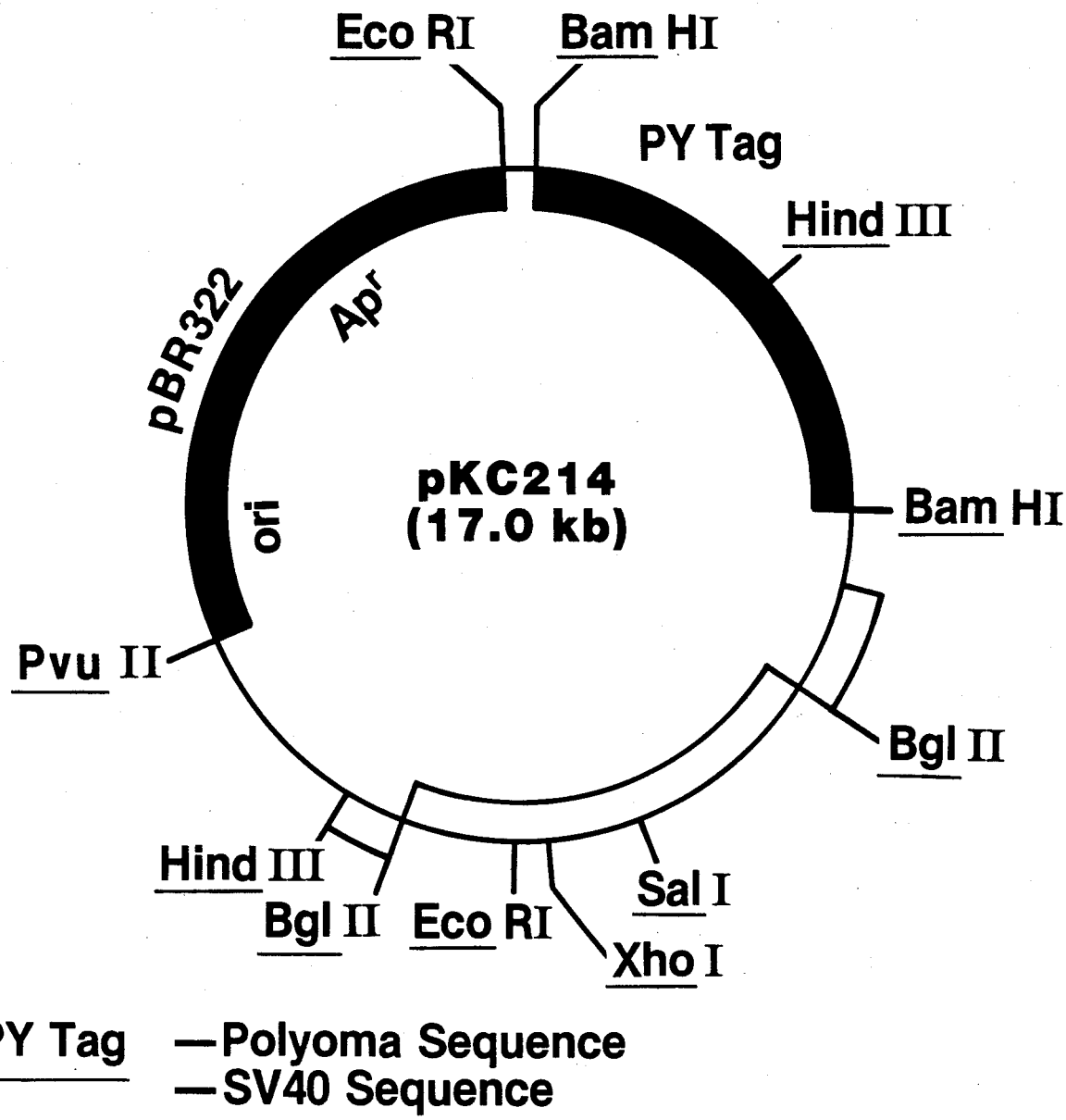
FIG. 3. The restriction site and functional map of plasmid pKC214.

The 7.5kb BglII restriction fragment of pKC203 comprises the structural genes and control elements for expression of resistance to antibiotics hygromycin B and G418. This fragment was ligated onto plasmid pSV5 gpt, a known plasmid whose construction is described in Mulligan and Berg, 1980, Science 209 (4463): 1422. Plasmid pSV5 gpt is approximately 9.3kb and contains both the origin of replication and the ampicillin resistance marker of plasmid pBR322 and also a functional SV40 early promoter which controls the transcription of a gene coding for xanthine-guanine phosphoribosyltransferase (gpt). A restriction site and functional map of plasmid pSV5 gpt is presented in FIG. 2 of the accompanying drawings. As will be apparent to those skilled in the art, plasmid pSV5 gpt can replicate both in *E. coli* and also in eukaryotic cells such as, for example, mammalian cells. Moreover, the unique BglII restriction site in plasmid pSV5 gpt allows for the direct ligation with the 7.5kb BglII restriction fragment of plasmid pKC203. Thus, the hygromycin B and G418 resistance conferring 7.5kb fragment can be ligated onto BglII treated plasmid pSV5 gpt. Since two possible orientations of the 7.5kb fragment are equally probable, the ligation of the 7.5kb fragment onto plasmid pSV5 gpt results in plasmids of two types, designated herein as plasmids pKC214 and pKC215. Restriction and functional maps of plasmids pKC214 and pKC215 are presented respectively in FIGS. 3 and 4 of the accompanying drawings.

In the illustrative plasmids pKC214 and pKC215, the eukaryotic promoter is adjacent to the genes, including the associated control elements, for hygromycin B and G418 resistance and is exemplified by the SV40 early promoter. The eukaryotic promoter controls the transcription and in part regulates the expression of the resistance genes when transformed into eukaryotic host cells. In addition, the present plasmids undergo chromosomal integration in eukaryotic hosts and therefore replicate along with and as part of the chromosomes during normal eukaryotic cell division.

Although the eukaryotic promoter herein exemplified in the illustrative plasmids pKC214 and pKC215 is the SV40 early promoter (O'Hare et al., 1981, Proc. Nat. Acad. Sci. USA 78(3) 1527, and Mulligan and Berg, 1980, Sci 209: 1422) many other eukaryotic promoters can also be used. Other illustrative eukaryotic promoters include, but are not limited to, the SV40 late promoter (Hamer and Leder, 1979, Nature 281: 35), HSVITK promoter (Pellicer et al., 1978, Cell 14: 133), adenovirus promoter (Thummel and Tjian, 1981, Cell 23: 825), adenovirus 2 (Ad 2) late promoter (Solnick, 1981, Cell 24: 135), polyoma promoter (Colantuoni et al., 1980, Proc. Nat. Acad. Sci. USA 77(7): 3850), mouse sarcoma virus promoter (VanBeveren et al., 1981, Nature 289: 258), yeast trp-1 promoter (Stinchcomb et al., 1979, Nature 282: 39), yeast leu 2 promoter (Ratzkin and Carbon, 1977, Proc. Nat. Acad. Sci. USA 74(2): 487, yeast his 3 promoter (Broach et al., 1979, Gene 8: 121), the yeast alcohol dehydrogenase promoter, and the yeast cytochrome c promoter (Guarente and Ptashne, 1981, Proc. Nat. Acad. Sci. USA 78(4): 2199).

While the construction of the illustrative plasmids pKC214 and pKC215 involved a BglII insertion into the pSV5 gpt gene downstream from the early SV40 promoter, other analogous constructions involving one or more of the above listed eukaryotic promoters can be made. For example, a BglII linear DNA fragment containing the hygromycin B and G418 resistance genes can be obtained from plasmid pKC203, or a derivative thereof, by treating the plasmid with BglII restriction enzyme according to conventional procedures. This fragment can be used directly or synthetic DNA linkers, known in the art, can be ligated to the resistance conferring fragment and the thus prepared fragment can be cloned downstream to an appropriate eukaryotic promoter such as, for example, the Ad 2 or the yeast cytochrome c promoter. Upon ligation with a prokaryotic replicon, these constructions, exemplified herein by plasmids pGD1, pGD2, pGD3, and pGD4, are functional in eukaryotic and prokaryotic host cells and are thus within the scope of the present invention. Moreover, it is understood and will be apparent to those skilled in the art that additional constructions involving different eukaryotic promoters can be made and that some eukaryotic promoters and constructions are preferred over others for use in certain hosts.

Figure 5:
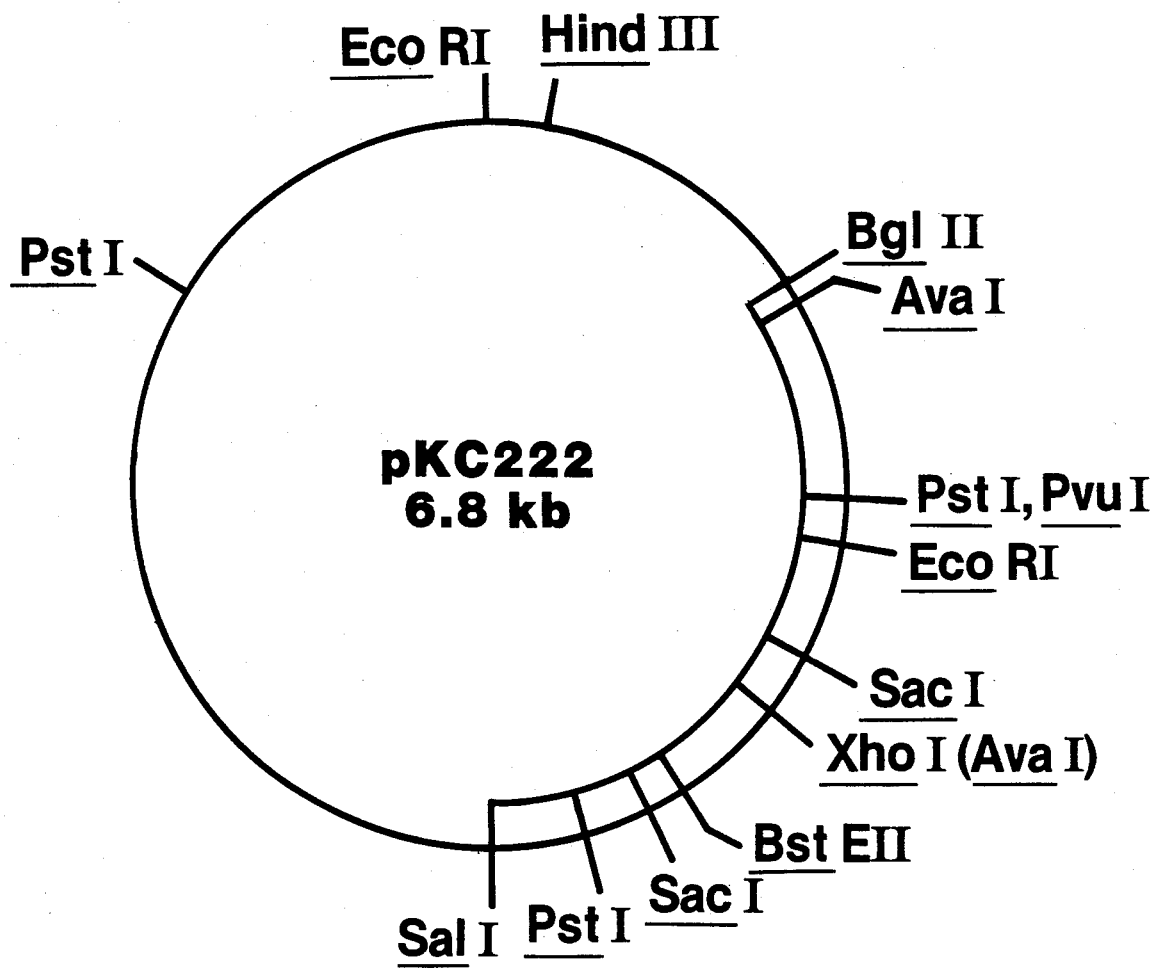
FIG. 5. The restriction site and functional map of plasmid pKC222.

The particular hygromycin B and G418 resistance genes and control elements, exemplified in illustrative plasmids pKC214, pKC215, pGD1, pGD2, pGD3 and pGD4, comprise the 7.5kb BglII fragment of plasmid pKC203. Moreover, within this BglII fragment, the DNA sequence that codes for resistance has been further localized to the 2.5kb SalI/BglII fragment. A restriction site map of the 2.5kb SalI/BglII fragment is presented as part of plasmid pKC222 in FIG. 5 of the accompanying drawings. Plasmid pKC222 is useful for isolating the individual genes and control elements that confer resistance to particular antibiotics. For example, the 1.51kb BglII/SacI fragment of plasmid pKC222 comprises the hygromycin B resistance gene and control element while the 1.65kg EcoRI/SalI fragment comprises the gene and control element that confers resistance to antibiotic G418. The latter gene and associated control element are believed to also simultaneously confer resistance to antibiotics apramycin and tobramycin in sensitive host cells such as, for example, *E. coli*.

The hygromycin B resistance gene and control element-containing 1.51kb BglII/SacI fragment comprises the DNA sequence

```
                                                                                   GA
                                                                                   ||
                                                                                   CT

GCT  CAT  GAG  CGG  AGA  ACG  AGA  TGA  CGT  TGG  AGG  GGC  AAG
|||  |||  |||  |||  |||  |||  |||  |||  |||  |||  |||  |||  |||
CGA  GTA  CTC  GCC  TCT  TGC  TCT  ACT  GCA  ACC  TCC  CCG  TTC

GTC  GCG  CTG  ATT  GCT  GGG  GCA  ACA  CGT  GGA  GCG  GAT  CGG
|||  |||  |||  |||  |||  |||  |||  |||  |||  |||  |||  |||  |||
CAG  CGC  GAC  TAA  CGA  CCC  CGT  TGT  GCA  CCT  CGC  CTA  GCC

GGA  TTG  TCT  TTC  TTC  AGC  TCG  CTG  ATG  ATA  TGC  TGA  CGC
|||  |||  |||  |||  |||  |||  |||  |||  |||  |||  |||  |||  |||
CCT  AAC  AGA  AAG  AAG  TCG  AGC  GAC  TAC  TAT  ACG  ACT  GCG

TCA  ATG  CCG  TTT  GGC  CTC  CGA  CTA  ACG  AAA  ATC  CCG  CAT
|||  |||  |||  |||  |||  |||  |||  |||  |||  |||  |||  |||  |||
AGT  TAC  GGC  AAA  CCG  GAG  GCT  GAT  TGC  TTT  TAG  GGC  GTA

TTG  GAC  GGC  TGA  TCC  GAT  TGG  CAC  GGC  GGA  CGG  CGA  ATG
|||  |||  |||  |||  |||  |||  |||  |||  |||  |||  |||  |||  |||
AAC  CTG  CCG  ACT  AGG  CTA  ACC  GTG  CCG  CCT  GCC  GCT  TAC

GCG  GAG  CAG  ACG  CTC  GTC  CGG  GGG  CAA  TGA  GAT  ATG  AAA
|||  |||  |||  |||  |||  |||  |||  |||  |||  |||  |||  |||  |||
CGC  CTC  GTC  TGC  GAG  CAG  GCC  CCC  GTT  ACT  CTA  TAC  TTT
                                                       MET  LYS

AAG  CCT  GAA  CTC  ACC  GCG  ACG  TCT  GTC  GAG  AAG  TTT  CTG
|||  |||  |||  |||  |||  |||  |||  |||  |||  |||  |||  |||  |||
TTC  GGA  CTT  GAG  TGG  CGC  TGC  AGA  CAG  CTC  TTC  AAA  GAC
LYS  PRO  GLU  LEU  THR  ALA  THR  SER  VAL  GLU  LYS  PHE  LEU

ATC  GAA  AAG  TTC  GAC  AGC  GTC  TCC  GAC  CTG  ATG  CAG  CTC
|||  |||  |||  |||  |||  |||  |||  |||  |||  |||  |||  |||  |||
TAG  CTT  TTC  AAG  CTG  TCG  CAG  AGG  CTG  GAC  TAC  GTC  GAG
ILE  GLU  LYS  PHE  ASP  SER  VAL  SER  ASP  LEU  MET  GLN  LEU

TCG  GAG  GGC  GAA  GAA  TCT  CGT  GCT  TTC  AGC  TTC  GAT  GTA
|||  |||  |||  |||  |||  |||  |||  |||  |||  |||  |||  |||  |||
AGC  CTC  CCG  CTT  CTT  AGA  GCA  CGA  AAG  TCG  AAG  CTA  CAT
SER  GLU  GLY  GLU  GLU  SER  ARG  ALA  PHE  SER  PHE  ASP  VAL
```

| | | | | | | | | | | | | |
|---|---|---|---|---|---|---|---|---|---|---|---|---|
| GGA | GGG | CGT | GGA | TAT | GTC | CTG | CGG | GTA | AAT | AGC | TGC | GCC |
| CCT | CCC | GCA | CCT | ATA | CAG | GAC | GCC | CAT | TTA | TCG | ACG | CGG |
| GLY | GLY | ARG | GLY | TYR | VAL | LEU | ARG | VAL | ASN | SER | CYS | ALA |

| | | | | | | | | | | | | |
|---|---|---|---|---|---|---|---|---|---|---|---|---|
| GAT | GGT | TTC | TAC | AAA | GAT | CGT | TAT | GTT | TAT | CGG | CAC | TTT |
| CTA | CCA | AAG | ATG | TTT | CTA | GCA | ATA | CAA | ATA | GCC | GTG | AAA |
| ASP | GLY | PHE | TYR | LYS | ASP | ARG | TYR | VAL | TYR | ARG | HIS | PHE |

| | | | | | | | | | | | | |
|---|---|---|---|---|---|---|---|---|---|---|---|---|
| GCA | TCG | GCC | GCG | CTC | CCG | ATT | CCG | GAA | GTG | CTT | GAC | ATT |
| CGT | AGC | CGG | CGC | GAG | GGC | TAA | GGC | CTT | CAC | GAA | CTG | TAA |
| ALA | SER | ALA | ALA | LEU | PRO | ILE | PRO | GLU | VAL | LEU | ASP | ILE |

| | | | | | | | | | | | | |
|---|---|---|---|---|---|---|---|---|---|---|---|---|
| GGG | GAA | TTC | AGC | GAG | AGC | CTG | ACC | TAT | TGC | ATC | TCC | CGC |
| CCC | CTT | AAG | TCG | CTC | TCG | GAC | TGG | ATA | ACG | TAG | AGG | GCG |
| GLY | GLU | PHE | SER | GLU | SER | LEU | THR | TYR | CYS | ILE | SER | ARG |

| | | | | | | | | | | | | |
|---|---|---|---|---|---|---|---|---|---|---|---|---|
| CGT | GCA | CAG | GGT | GTC | ACG | TTG | CAA | GAC | CTG | CCT | GAA | ACC |
| GCA | CGT | GTC | CCA | CAG | TGC | AAC | GTT | CTG | GAC | GGA | CTT | TGG |
| ARG | ALA | GLN | GLY | VAL | THR | LEU | GLN | ASP | LEU | PRO | GLU | THR |

| | | | | | | | | | | | | |
|---|---|---|---|---|---|---|---|---|---|---|---|---|
| GAA | CTG | CCC | GCT | GTT | CTG | CAG | CCG | GTC | GCG | GAG | GCC | ATG |
| CTT | GAC | GGG | CGA | CAA | GAC | GTC | GGC | CAG | CGC | CTC | CGG | TAC |
| GLU | LEU | PRO | ALA | VAL | LEU | GLN | PRO | VAL | ALA | GLU | ALA | MET |

| | | | | | | | | | | | | |
|---|---|---|---|---|---|---|---|---|---|---|---|---|
| GAT | GCG | ATC | GCT | GCG | GCC | GAT | CTT | AGC | CAG | ACG | AGC | GGG |
| CTA | CGC | TAG | CGA | CGC | CGG | CTA | GAA | TCG | GTC | TGC | TCG | CCC |
| ASP | ALA | ILE | ALA | ALA | ALA | ASP | LEU | SER | GLN | THR | SER | GLY |

| | | | | | | | | | | | | |
|---|---|---|---|---|---|---|---|---|---|---|---|---|
| TTC | GGC | CCA | TTC | GGA | CCG | CAA | GGA | ATC | GGT | CAA | TAC | ACT |
| AAG | CCG | GGT | AAG | CCT | GGC | GTT | CCT | TAG | CCA | GTT | ATG | TGA |
| PHE | GLY | PRO | PHE | GLY | PRO | GLN | GLY | ILE | GLY | GLN | TYR | THR |

| | | | | | | | | | | | | |
|---|---|---|---|---|---|---|---|---|---|---|---|---|
| ACA | TGG | CGT | GAT | TTC | ATA | TGC | GCG | ATT | GCT | GAT | CCC | CAT |
| TGT | ACC | GCA | CTA | AAG | TAT | ACG | CGC | TAA | CGA | CTA | GGG | GTA |
| THR | TRP | ARG | ASP | PHE | ILE | CYS | ALA | ILE | ALA | ASP | PRO | HIS |

| | | | | | | | | | | | | |
|---|---|---|---|---|---|---|---|---|---|---|---|---|
| GTG | TAT | CAC | TGG | CAA | ACT | GTG | ATG | GAC | GAC | ACC | GTC | AGT |
| CAC | ATA | GTG | ACC | GTT | TGA | CAC | TAC | CTG | CTG | TGG | CAG | TCA |
| VAL | TYR | HIS | TRP | GLN | THR | VAL | MET | ASP | ASP | THR | VAL | SER |

| | | | | | | | | | | | | |
|---|---|---|---|---|---|---|---|---|---|---|---|---|
| GCG | TCC | GTC | GCG | CAG | GCT | CTC | GAT | GAG | CTG | ATG | CTT | TGG |
| CGC | AGG | CAG | CGC | GTC | CGA | GAG | CTA | CTC | GAC | TAC | GAA | ACC |
| ALA | SER | VAL | ALA | GLN | ALA | LEU | ASP | GLU | LEU | MET | LEU | TRP |

-continued

```
GCC GAG GAC TGC CCC GAA GTC CGG CAC CTC GTG CAC GCG
||| ||| ||| ||| ||| ||| ||| ||| ||| ||| ||| ||| |||
CGG CTC CTG ACG GGG CTT CAG GCC GTG GAG CAC GTG CGC
ALA GLU ASP CYS PRO GLU VAL ARG HIS LEU VAL HIS ALA

GAT TTC GGC TCC AAC AAT GTC CTG ACG GAC AAT GGC CGC
||| ||| ||| ||| ||| ||| ||| ||| ||| ||| ||| ||| |||
CTA AAG CCG AGG TTG TTA CAG GAC TGC CTG TTA CCG GCG
ASP PHE GLY SER ASN ASN VAL LEU THR ASP ASN GLY ARG

ATA ACA GCG GTC ATT GAC TGG AGC GAG GCG ATG TTC GGG
||| ||| ||| ||| ||| ||| ||| ||| ||| ||| ||| ||| |||
TAT TGT CGC CAG TAA CTG ACC TCG CTC CGC TAC AAG CCC
ILE THR ALA VAL ILE ASP TRP SER GLU ALA MET PHE GLY

GAT TCC CAA TAC GAG GTC GCC AAC ATC TTC TTC TGG AGG
||| ||| ||| ||| ||| ||| ||| ||| ||| ||| ||| ||| |||
CTA AGG GTT ATG CTC CAG CGG TTG TAG AAG AAG ACC TCC
ASP SER GLN TYR GLU VAL ALA ASN ILE PHE PHE TRP ARG

CCG TGG TTG GCT TGT ATG GAG CAG CAG ACG CGC TAC TTC
||| ||| ||| ||| ||| ||| ||| ||| ||| ||| ||| ||| |||
GGC ACC AAC CGA ACA TAC CTC GTC GTC TGC GCG ATG AAG
PRO TRP LEU ALA CYS MET GLU GLN GLN THR ARG TYR PHE

GAG CGG AGG CAT CCG GAG CTT GCA GGA TCG CCG CGG CTC
||| ||| ||| ||| ||| ||| ||| ||| ||| ||| ||| ||| |||
CTC GCC TCC GTA GGC CTC GAA CGT CCT AGC GGC GCC GAG
GLU ARG ARG HIS PRO GLU LEU ALA GLY SER PRO ARG LEU

CGG GCG TAT ATG CTC CGC ATT GGT CTT GAC CAA CTC TAT
||| ||| ||| ||| ||| ||| ||| ||| ||| ||| ||| ||| |||
GCC CGC ATA TAC GAG GCG TAA CCA GAA CTG GTT GAG ATA
ARG ALA TYR MET LEU ARG ILE GLY LEU ASP GLN LEU TYR

CAG AGC TTG GTT GAC GGC AAT TTC GAT GAT GCA GCT TGG
||| ||| ||| ||| ||| ||| ||| ||| ||| ||| ||| ||| |||
GTC TCG AAC CAA CTG CCG TTA AAG CTA CTA CGT CGA ACC
GLN SER LEU VAL ASP GLY ASN PHE ASP ASP ALA ALA TRP

GCG CAG GGT CGA TGC GAC GCA ATC GTC CGA TCC GGA GCC
||| ||| ||| ||| ||| ||| ||| ||| ||| ||| ||| ||| |||
CGC GTC CCA GCT ACG CTG CGT TAG CAG GCT AGG CCT CGG
ALA GLN GLY ARG CYS ASP ALA ILE VAL ARG SER GLY ALA

GGG ACT GTC GGG CGT ACA CAA ATC GCC CGC AGA AGC GCG
||| ||| ||| ||| ||| ||| ||| ||| ||| ||| ||| ||| |||
CCC TGA CAG CCC GCA TGT GTT TAG CGG GCG TCT TCG CGC
GLY THR VAL GLY ARG THR GLN ILE ALA ARG ARG SER ALA

GCC GTC TGG ACC GAT GGC TGT GTA GAA GTA CTC GCC GAT
||| ||| ||| ||| ||| ||| ||| ||| ||| ||| ||| ||| |||
CGG CAG ACC TGG CTA CCG ACA CAT CTT CAT GAG CGG CTA
ALA VAL TRP THR ASP GLY CYS VAL GLU VAL LEU ALA ASP
```

```
AGT GGA AAC CGA CGC CCC AGC ACT CGT CCG AGG GCA AAG
 |||  |||  |||  |||  |||  |||  |||  |||  |||  |||  |||  |||  |||
TCA CCT TTG GCT GCG GGG TCG TGA GCA GGC TCC CGT TTC
SER GLY ASN ARG ARG PRO SER THR ARG PRO ARG ALA LYS

GAA TAG AGT AGA TGC CGA CCG AAC AAG AGC TGA TTT CGA
 |||  |||  |||  |||  |||  |||  |||  |||  |||  |||  |||  |||  |||
CTT ATC TCA TCT ACG GCT GGC TTG TTC TCG ACT AAA GCT
GLU

GAA CGC CTC AGC CAG CAA CTC GCG CGA GCC TAG CAA GGC
 |||  |||  |||  |||  |||  |||  |||  |||  |||  |||  |||  |||  |||
CTT GCG GAG TCG GTC GTT GAG CGC GCT CGG ATC GTT CCG

AAA TGC GAG AGA ACG GCC TTA CGC TTG GTG GCA CAG TTC
 |||  |||  |||  |||  |||  |||  |||  |||  |||  |||  |||  |||  |||
TTT ACG CTC TCT TGC CGG AAT GCG AAC CAC CGT GTC AAG

TCG TCC ACA GTT CGC TAA GCT CGC TCG GCT GGG TCG CGG
 |||  |||  |||  |||  |||  |||  |||  |||  |||  |||  |||  |||  |||
AGC AGG TGT CAA GCG ATT CGA GCG AGC CGA CCC AGC GCC

GAG GGC CGG TCG CAG TGA TTC AGG CCC TTC TGG ATT GTG
 |||  |||  |||  |||  |||  |||  |||  |||  |||  |||  |||  |||  |||
CTC CCG GCC AGC GTC ACT AAG TCC GGG AAG ACC TAA CAC

TTG GTC CCC AGG GCA CGA TTG TCA TGC CCA CGC ACT CGG
 |||  |||  |||  |||  |||  |||  |||  |||  |||  |||  |||  |||  |||
AAC CAG GGG TCC CGT GCT AAC AGT ACG GGT GCG TGA GCC

GTG ATC TGA CTG ATC CCG CAG ATT GGA GAT CGC CGC CCG
 |||  |||  |||  |||  |||  |||  |||  |||  |||  |||  |||  |||  |||
CAC TAG ACT GAC TAG GGC GTC TAA CCT CTA GCG GCG GGC

TGC CTG CCG ATT GGG TGC AGA TCT
 |||  |||  |||  |||  |||  |||  |||  |||
ACG GAC GGC TAA CCC ACG TCT AGA
``` wherein
A is deoxyadenyl,
G is deoxyguanidyl,
C is deoxycytisyl and
T is thymidyl.

The hygromycin B resistance gene codes for the enzyme hygromycin B phosphotransferase. The amino acids, which comprise the hygromycin B phosphotransferase enzyme, are specified below the appropriate nucleotide triplet and are conventionally abbreviated.

Accordingly,
MET is methionine,
LYS is lysine,
PRO is proline,
GLU is glutamic acid,
LEU is leucine,
THR is threonine,
ALA is alanine,
SER is serine,
VAL is valine,
PHE is phenylalanine,
ILE is isoleucine,
GLY is glycine,
ASP is aspartic acid,
GLU is glutamine,
ARG is arginine,
CYS is cysteine,
TRP is tryptophan,
ASN is asparagine,
HIS is histidine, and
TYR is tyrosine.

The hygromycin B resistance gene or the entire BglII/SacI fragment can be conventionally synthesized by the modified phosphotriester method using fully protected trideoxyribonucleotide building blocks in substantial accordance with the procedure of Itakura et al., 1977, Science 198: 1056 and Crea et al., 1978, Proc. Nat. Acad. Sci. USA 75: 5765. Skilled artisans can construct still other hygromycin B resistance genes that encode the same hygromycin B phosphotransferase enzyme by substituting nucleotides in accordance with the genetic code.

Recombinant DNA cloning vectors that confer resistance to one, more than one, or all of the aforementioned antibiotics can be constructed by cloning an appropriate plasmid pKC203, pKC222 or synthetic DNA fragment downstream to an appropriate eukaryotic promoter. Upon being provided with a prokaryotic replicon, the vectors, exemplified herein by plasmids pGD10, pGD11, pGD12, pGD13, pGD14, and pGD15, are functional in both eukaryotic and prokaryotic host cells and are thus within the scope of the present invention. It will be understood that the present invention is in no way limited by the above postulated additional resistance conferring activity of the G418 resistance gene.

The 7.5kb BglII fragment of plasmid pKC203 also contains a prokaryotic replicon and therefore can be self ligated to form a plasmid. The resulting plasmid, designated as pSC701, is functional in *E. coli* and is useful for generating derivative plasmids which are useful as starting materials. Thus, plasmid pSC701 DNA can be HaeII digested and then ligated to produce plasmids pKC257 and pKC259. Plasmid pKC257 is ~4.2kb and confers resistance to hygromycin B while plasmid pKC259 is ~5.0kb and confers resistance to both hygromycin B and apramycin. Sau3AI digestion of plasmid pKC257 DNA followed by ligation results in a still smaller plasmid, designated as pKC261. This plasmid also confers resistance to hygromycin B.

The above derivative plasmids are functional in *E. coli* and are useful as starting material for constructing vectors of the present invention. Thus, insertion of plasmid pKC259 into pSV5 gpt results in plasmids pLO314 and pLO315; insertion of plasmid pKC257 into pSV5 gpt results in plasmids pLO316 and pLO317; and insertion of plasmid pKC261 into pSV5 gpt results in plasmids pLO318 and pLO319. All of the aforementioned pLO plasmids are functional in both prokaryotic and eukaryotic host cells and thus are within the scope of the present invention.

Additional plasmid starting materials can also be constructed. For example, insertion of the plac-containing HaeII restriction fragment of plasmid pUR222, (the construction of which is disclosed in Rüther, 1981, Nucleic Acids Research 9: 4087), into plasmid pKC261 results in plasmid pKC275. The latter plasmid is ~3.6kb, confers resistance to hygromycin B, and can be inserted into plasmid pSV5 gpt to form illustrative plasmids pLO320 and pLO321. Furthermore, insertion of a 2μ DNA-containing restriction fragment of plasmid YEp24 into pKC259 results in plasmid pKC264, insertion of the ~2.5kb BglII/SalI fragment of pKC259 into appropriately cut Yep24 results in plasmid pKC273, and insertion of the ~3.2kb PstI fragment of plasmid pKC264 into pBR322 results in plasmid pLO378. Both plasmids pLO378 and pKC273 are functional in yeast and *E. coli* and consequently are within the scope of the present invention. Construction of the aforementioned and other vectors using the foregoing plasmid starting materials is further and more specifically disclosed in Examples 25 to 42 below.

It will be understood that those of ordinary skill can construct or isolate still other DNA sequences that also confer resistance to hygromycin B and G418, either individually or in combination, and that these sequences can be used in place of the resistance genes and control elements exemplified herein. Moreover, functional derivatives of the 7.5 kb BglII fragment or the 2.5 kb SalI/BglII fragment can be constructed by adding, eliminating, or substituting certain nucleotides in accordance with the genetic code. Those of ordinary skill will understand that use of such derivatives and also other hygromycin B and G418-conferring DNA segments results in vectors that are within the scope of the present invention.

Although the prokaryotic replicon exemplified herein in the illustrative plasmids is the plasmid pBR322 replicon, many other replicons can also be used for making similar constructions. Other illustrative prokaryotic replicons include, but are not limited to, the pMB1 replicon (Betlach et al., 1976, Fed. Proc. 35: 2037), NR1 replicon (Rownd and Mickel, 1971 Nature 234: 40), RK2 replicon (Beringer, 1974, J. Gen. Microbiol. 84: 188), R6K replicon (Kontomichalou et al., 1970, J. Bacteriol. 104: 34), pSC101 replicon (Cohen and Chang, 1977, J. Bacteriol. 132: 734), RP1 replicon (Grinsted et al., 1972, J. Bacteriol. 110: 529), RP4 replicon (1977, Nagahari et al., Gene 1: 141)), RSF1010 replicon (Guerry et al., 1974, J. Bacteriol. 117: 619), PUB110 replicon (Gryczan, et al., 1978, J. Bacteriol. 134: 318), and the SLP1.2 replicon (Bibb et al., Nature 284: 526). It is understood and will be apparent to those skilled in the art that many additional prokaryotic replicons can be constructed and that generally some prokaryotic replicons are preferred and will be selected over others for use in certain hosts. For example, the RSF1010, PUB110, and the SLP1.2 replicons are respectively preferred for use in Pseudomonas, Bacillus and Streptomyces, while the other replicons cited above are preferred for use in *E. coli*.

The vectors of the present invention are highly versatile and are functional in almost any prokaryotic or eukaryotic host cell. The only requirements are (1) that the host cell be capable of division and culture; (2) that the host cell be competent for transformation; and (3) that the non-transformed host cell be sensitive to and thus killed by either or both hygromycin B and G418. Therefore, the present vectors are useful in bacteria, fungi, yeast, plant cells, animal cells, and free living unicellular eukaryotes.

The wealth of genetic and biochemical information about *E. coli* K12 makes it a convenient and preferred prokaryotic host cell for purposes of the present invention. Other preferred prokaryotic host cells are bacteria, including but not limited to *E. coli*, *E. coli* K12 BE827, Bacillus, *Bacillus subtilis*, Pseudomonas, Agrobacterium, Streptomyces, Staphylococcus, Streptococcus, Actinomycetes, and Serratia; and blue-green algae. Preferred eukaryotic host cells are fungi, including but not limited to Neurospora, Cephalosporium, Aspergillus, Penicillium, and yeast; cells susceptible to culture that are derived from tissue of multicellular organisms, including but not limited to a mammalian cell, murine mammalian cell, mouse cell, Mouse Ltk⁻ cell, human cell, avian cell, amphibian cell, reptilian cell, a cell derived from a member of the phylum Chordata, an animal cell, a plant cell, a gymnospermous cell, an angiospermous cell; and free living unicellular organisms, including but not limited to algae and protozoans.

As described above, the vectors of the present invention are functional in virtually any type of prokaryotic or eukaryotic host cell and confer the desired antibiotic resistance to hygromycin B and G418 sensitive cells such as, for example, *E. coli* K12 BE827, *E. coli* K12 BE783, *E. coli* K12 BE1041, Mouse Ltk⁻ cells, and *Saccharomyces cerevisiae*. Thus, the transformants of the present invention, including but not limited to illustrative transformants *E. coli* K12 BE827/pKC214, *E. coli* K12 BE827/pKC215, Mouse Ltk⁻/pKC214, Mouse Ltk⁻/pKC215, *E. coli* K12 BE783/pKC273, and *Saccharomyces cerevisiae*/pKC273, express resistance to either or both of the aforementioned antibiotics and are therefore useful, under appropriate selection conditions, for propagating and maintaining the present vectors. Those skilled in the art will further recognize that non-selectable structural genes can be cloned into the vectors and that, following transformation and subsequent culturing under hygromycin B or G418 selection pressure in mammalian or other host cells, the cloned genes can be stabilized, maintained, and expressed. Only host cells thus transformed can survive in the presence of hygromycin B or G418 so therefore, the vectors of the present invention allow for the easy isolation and initial identification of transformants.

The large number of host cells that can be transformed with the vectors of the present invention is important because it allows for the easy amplification and manipulation of eukaryotic vectors in prokaryotic host cells. This is particularly advantageous because the genetic background of prokaryotes, such as *E. coli* and the like, is well known and conventional recombinant DNA procedures are applicable and can be conveniently done in such systems. Consequently, the present recombinant DNA cloning vectors, including those that contain selectable or non-selectable structural genes, can be first manipulated and amplified in prokaryotic cells and then transformed into eukaryotic host cells for expression, thus avoiding the serious problems associated with being restricted exclusively to eukaryotic systems.

While all the embodiments of the present invention are useful, some of the present recombinant DNA cloning vectors and transformants are preferred. Accordingly, preferred vectors are plasmids pKC214, pKC215, and pKC273; preferred prokaryotic transformants are *E. coli* K12 BE827/pKC214, *E. coli* K12 BE827/pKC215, and *E. coli* K12 BE783/pKC273; and preferred eukaryotic transformants are Mouse Ltk⁻/pKC214, Mouse Ltk⁻/pKC215, and *Saccharomyces cerevisiae*/pKC273.

The utility of the vectors and transformants of the present invention is broad and allows for the greater and more rapid application of recombinant DNA technology to eukaryotic systems. For example, the ability of the present vectors, including plasmids, bacteriophages, and viruses, to confer resistance to antibiotics that are toxic to both eukaryotic and prokaryotic cells provides a functional test for selecting transformants. This is important because such a test is a practical necessity for determining and selecting the particular cells that have acquired vector DNA. Additional DNA sequences, that lack functional tests for their presence, can be inserted onto the present vectors and then transformants containing the non-selectable DNA can be isolated by hygromycin B or G418 selection. Such non-selectable DNA sequences include, but are not limited to, genes that specify a post-translationally modified protein such as, for example, fibronectin or hepatitis B antigen, both of which are post-translationally glycosylated by eukaryotic cells.

More particularly a non-selectable gene sequence can be inserted, for example, into the PvuI site of plasmids, such as, for example, illustrative plasmids pGD14 and pGD15, that contain the 2.75kb SalI/BglII restriction fragment of plasmid pKC203. Such an insertion inactivates the hygromycin B resistance gene and thus allows for the easy identification of transformants containing the recombinant plasmid. This is done by first selecting for G418 resistance and, secondarily, identifying those G418 resistant transformants that are not resistant to hygromycin B. In a similar manner, insertion of a gene sequence of interest at, for example, the XhoI site inactivates the G418 resistance gene. Thus transformants carrying this recombinant plasmid also can be identified easily by first selecting for hygromycin B resistance and, secondarily, identifying those hygromycin B transformants that are not resistant to G418. Therefore, the ability to select for antibiotic resistance in eukaryotic or prokaryotic transformants allows for the efficient isolation of the extremely rare cells that contain the particular non-selectable DNA of interest.

The functional test for antibiotic resistance, as described herein above, can also be used to identify DNA sequences that act as control elements and direct expression of an individual antibiotic resistance gene. Such sequences, including but not limited to promoters, attenuators, repressors, inducers, ribosomal binding sites, and the like, can be used to control the expression of other structural genes in both eukaryotic and prokaryotic cells.

The hygromycin B and G418 resistance-conferring vectors of the present invention are also useful for stabilizing linked DNA sequences of various sorts. These genes or fragments, covalently linked to the hygromycin B or G418 resistance gene and propagated either in eukaryotes or prokaryotes, can be maintained by exposing the transformants to levels of hygromycin B or G418 that are toxic to non-transformed cells. Therefore, transformants that lose the vector, and consequently any covalently linked DNA, die and are eliminated from the culture. Thus, the vectors of the present invention can stabilize and maintain any DNA sequence of interest.

The cloning vectors and transformants of the present invention not only provide for the commercially feasible production of both unmodified and post-translationally modified polypeptides in eukaryotic cells, but also for improved yields of various products that are currently produced in prokaryotic and eukaryotic cells. Examples of such products include, but are not limited to, Streptomycin, Tylosin, Cephalosporins, Actaplanin, biosynthetic insulin, biosynthetic human insulin, biosynthetic human proinsulin, biosynthetic interferon, and biosynthetic human interferon. The present invention also provides selectable vectors that can be used to identify, characterize, and reconstruct DNA sequences that code for (1) commercially important proteins, (2) enzymatic functions in metabolic pathways leading to commercially important processes and compounds, or (3) control elements that improve gene expression. These desired DNA sequences include, but are not limited to, DNA that codes for the biodegradation of hydrocarbons, for derivatized antibiotics such as, for example, Cephalosporin, Tylosin, and Actaplanin derivatives, or for enzymes that mediate and increase bioproduction of antibiotics or other products. The capability for inserting and stabilizing such DNA sequences in eukaryotic and prokaryotic cells is important because the production, using recombinant DNA methodology, of certain antibiotics and post-translationally modified proteins requires a eukaryotic host. Moreover, the ability of the present vectors to be functional in prokaryotic cells such as, for example, *E. coli*, allows for their easy manipulation and amplification, thus circumventing the problems associated with eukaryotic cells in which such procedures are difficult if not impossible to do.

The present invention further provides for the construction of new varieties or strains of multicellular organisms that can better tolerate a vigorous regimen of antibiotics designed to eliminate internal parasites, pathogenic bacteria, and other infectious agents. For example, the hygromycin B or G418 resistance genes of the present invention can be inserted, individually or in combination, into germline or early embryonic cells to create multicellular organisms that are highly resistant to the antibiotics. Therefore, resistant multicellular varieties such as, for example, swine, cattle, and sheep, can be made to better tolerate the higher levels of antibiotics that are required for improved control of harmful parasites and infectious disease causing agents that slow growth and reduce vitality.

The following examples further illustrate and detail the invention disclosed. Plasmids pSV5 gpt, pLG669, p04 and pKC7, that are needed to construct the present invention, are publically available and/or susceptible to construction in accordance with the literature procedures that are cited. Starting materials that are not so available or susceptible to construction have been deposited with the American Type Culture Collection or the Northern Regional Research Laboratory. The accession numbers and also an explanation of and the actual procedures for constructing both the starting materials and the present invention are described where appropriate.

EXAMPLE 1

Plasmid pKC203

A. Isolation of Plasmid DNA From *E. coli* JR225

The bacterium *E. coli* JR225 (ATCC No. 31912) was cultured in TY broth (1% tryptone, 0.5% yeast extract, 0.5% sodium chloride, pH 7.4) with 100 µg/ml. of antibiotic hygromycin B according to conventional microbiological procedures. After 18 hours incubation, about 0.5 ml. of the culture was transferred to a 1.5 ml Eppendorf tube and centrifuged for about 15 seconds. Unless otherwise indicated, all the manipulations were done at ambient temperature. The resultant supernatant was carefully removed with a finetip aspirator and the cell pellet was suspended in about 100 µl. of freshly prepared lysozyme solution which contained 2 mg./ml. lysozyme, 50 mM glucose, 10 mM CDTA (cyclohexane diaminetetracetate) and 25 mM Tris-HCl (pH 8.0). After incubation at 0° C. for 30 minutes about 200 µl. of alkaline SDS (sodium dodecyl sulfate) solution (0.2N NaOH, 1% SDS) was added and the tube was gently vortexed and then maintained at 0° C. for 15 minutes. Next about 150 µl. of 3M sodium acetate (prepared by dissolving 3 moles of sodium acetate in a minimum of water, adjusting the pH to 4.8 with glacial acetic acid, and then adjusting the volume to 1 l.) was added and the contents of the tube were then mixed gently by inversion for a few seconds during which time a DNA clot formed.

The tube was maintained at 0° C. for 60 minutes and then centrifuged for 5 minutes to yield an almost clear supernatant. About 0.4 ml of the supernatant was transferred to a second centrifuge tube to which 1 ml. of cold ethanol was added. After the tube was held at −20° C. for 30 minutes, the resultant precipitate was collected by centrifugation (2 minutes) and the supernatant was removed by aspiration. The thus collected pellet was dissolved in 100 µl. of 0.1M sodium acetate/0.05M Tris-HCl (pH 8) and was reprecipitated by the addition of 2 volumes of cold ethanol. After 10 minutes at 20° C., the precipitate was collected by centrifugation, as described above, and constitutes the desired *E. coli* JR225 plasmid DNA.

B. Transformation of *E. coli* JR225 Plasmid DNA and Isolation of Plasmid pKC203

The *E. coli* JR225 plasmid DNA pellet was dissolved in about 100 µl. of 0.1M sodium acetate/0.05M Tris-HCl (pH 8) and precipitated with 2 volumes of cold ethanol. The resultant plasmid DNA, was collected and then dissolved in about 40 µl. of water or dilute buffer, and finally used to transform *E. coli* K12 BE827 in substantial accordance with the transformation method of Wensink, 1974, Cell 3: 315. *E. coli* K12 BE827 has been deposited and made part of the stock culture collection of the American Type Culture Collection, Rockville, Md., from which it is available to the public without restriction under the number ATCC 31911. The resultant transformants were selected on TY agar (1% tryptone, 0.5% yeast extract, 0.5% sodium chloride, 1.5% agar, pH 7.4) containing 200 µg/ml of antibiotic hygromycin B. Some of the transformants, as shown by gel electrophoresis (Rao and Rogers, 1978) and other tests, contained both large and smaller (15kb) plasmids and were resistant to both antibiotics ampicillin and hygromycin B. Other transformants contained only the smaller 15kb plasmid and were resistant to antibiotics hygromycin B and G418 but were sensitive to ampicillin.

Transformants of the latter type were plated on TY agar containing 1 mg./ml. of antibiotic hygromycin B and were cultured using standard microbiological techniques. The resultant cells were used, according to the procedure of Example 1A, to isolate the above described 15kb hygromycin B and G418 resistance conferring plasmid, hereinafter designated as plasmid pKC203. The presence of the antibiotic hygromycin B and G418 resistance genes on plasmid pKC203 was confirmed by subsequent transformation and selection analysis.

EXAMPLE 2

Isolation of the Antibiotic Hygromycin B And G418 Resistance Genes and Control Elements About 5 µg. of plasmid pKC203 DNA were treated with BglII restriction enzyme according to the instructions and under the conditions specified by the manufacturer*. Of the 7.5kb, 5.8kb, and 0.5kb fragments recovered, the 7.5kb BglII fragment contained the desired antibiotic hygromycin B and G418 resistance genes and control elements. This was confirmed by subsequent transformation and selection analysis which showed that cells that are normally sensitive to antibiotics hygromycin B and G418 are resistant to the antibiotics upon transformation with the 7.5kb BglII fragment.

*Restriction enzymes and instructions can be readily obtained from the following sources:
Bethesda Research Laboratories Inc.
Box 6010
Rockville, Md 20850.
Boehringer Mannheim Biochemicals
7941 Castleway Drive
P.O. Box 50816
Indianapolis, Ind. 46250.
New England Bio Labs., Inc.
283 Cabot
Beverly, Mass. 01915.
Research Products
Miles Laboratories Inc.
Elkhart, Ind. 46515.

EXAMPLE 3

Construction of Plasmids pKC214 and pKC215 and Transformants *E. coli* K12 BE827/pKC214 and *E. coli* K12 BE827/pKC215

Plasmid pSV5 gpt, the construction of which is described in Mulligan and Berg, 1980, Science 209(4463): 1422, has a unique BglII site within the gpt gene. Cloning as described below, allows for the expression of the antibiotic hygromycin B and G418 resistance genes.

About 5 μg. of plasmid pSV5 gpt DNA were treated with BglII restriction enzyme according to the instructions and under the conditions specified by the manufacturer. After the enzyme was inactivated by heating at 70° C. for 5 minutes, about 1 μg of the DNA was mixed in a 1:1 ratio with the 7.5kb BglII fragment of pKC203. The fragments were joined using T4 DNA ligase according to the instructions and under the conditions specified by the manufacturer*.

Figure 4:
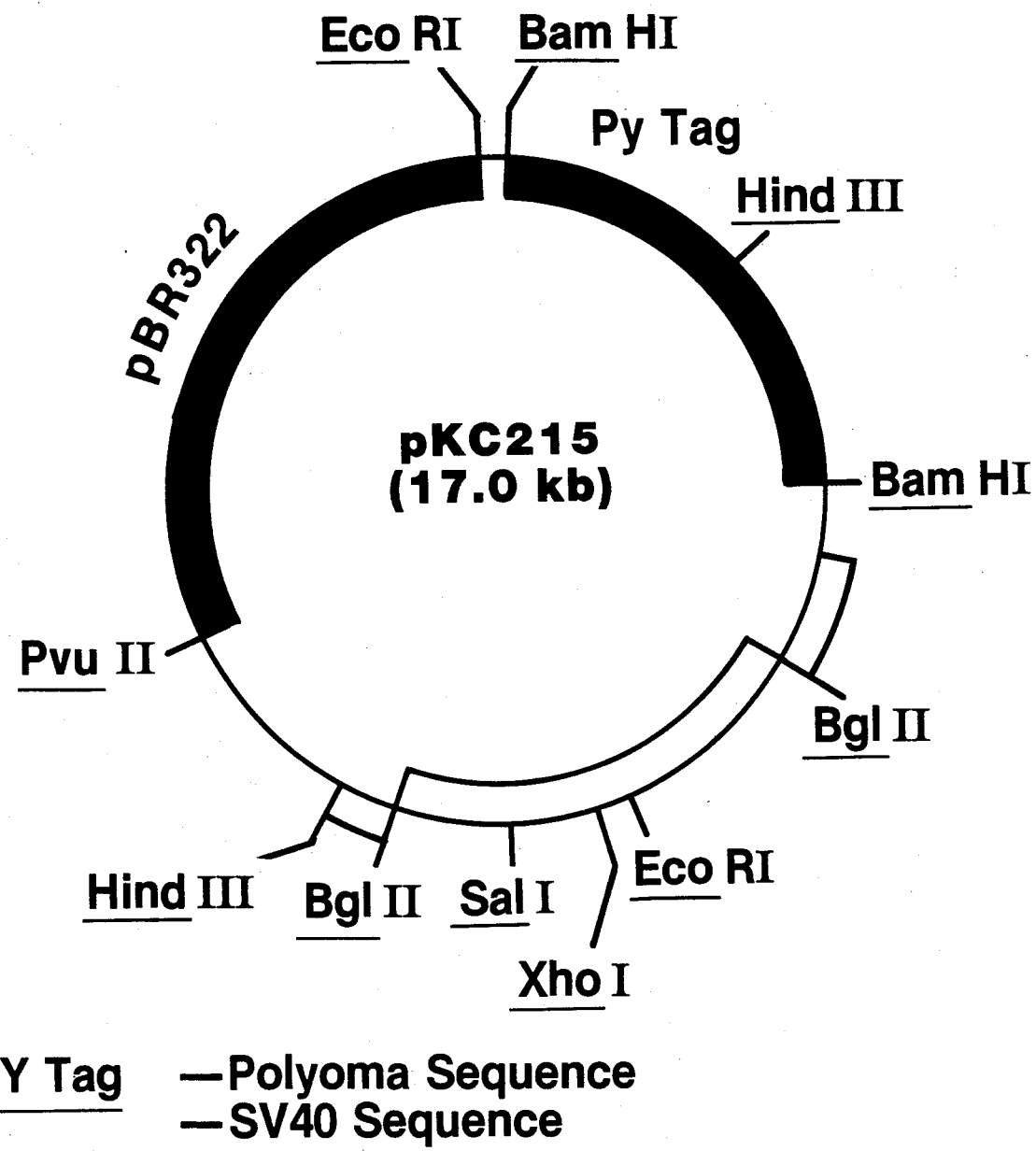
FIG. 4. The restriction site and functional map of plasmid pKC215.

*T4 DNA ligase and instructions can be readily obtained from the following source:
Bethesda Research Laboratories
Box 6010
Rockville, Md 20850.
The ligated mixture was used to transform *E. coli* K12 BE827 in substantial accordance with the transformation method of Wensink, 1974, Cell 3: 315, on TY plates containing 100 μg/ml. each of antibiotics ampicillin and apramycin. The recombinant clones were plated on TY plates containing 100 μg./ml. of ampicillin and 200 μg./ml. of antibiotic hygromycin B. About half of the antibiotic hygromycin B resistant recombinant clones contained plasmid pKC214 (FIG. 3) while the remainder contained plasmid pKC215 (FIG. 4).

Plasmid DNA from various of the above clones was isolated, according to the procedure of Example 1A, and conventionally distinguished by restriction enzyme analysis. In this way, the constructed plasmids pKC214 and pKC215 and the constructed transformants *E. coli* K12 BE827/pKC214 and *E. coli* K12 BE827/pKC215 were identified and subsequently isolated for future use.

EXAMPLE 4

Construction of Mouse Ltk−/pKC214

Mouse Ltk− cells were conventionally cultured for regular cell maintenance in a medium comprising minimum essential medium with Earle's salts and nonessential amino acids (Eagle, 1959, Science 130: 432), 10% v/v newborn calf serum, and 292 μg./ml. glutamine. The thus cultured Mouse Ltk− cells were then transformed with plasmid pKC214 in substantial accordance with the protocol described in Wigler et al., 1979, Proc. Nat. Acad. Sci. USA 76(3): 1373, except that (1) 100–300 ng. of plasmid DNA was added to each plate in 1 ml. of calcium phosphate precipitate; and (2) the culture medium was as described above. After 4 hours incubation at 37° C., the medium was replaced with fresh medium and the cells were allowed to incubate for an additional 20 hours. At that time antibiotic hygromycin B selection pressure was applied. This was done by changing the medium to a selection medium which contained the above described medium and also about 75–1000 μg./ml. of antibiotic hygromycin B. The concentration of the antibiotic that is preferred for the selecting medium is 200 μg./ml. The selecting medium was changed after the first day, then two days after that, and finally after every third day over the 2-3 weeks in which transformant clones arose. Colonies were harvested by hand using a pipette and were grown into mass culture under continued selection pressure. The thus cultured antibiotic hygromycin B resistant cells constitute the desired Mouse Ltk−/pKC214 transformants.

EXAMPLE 5

Construction of Mouse Ltk−/pKC215

Mouse Ltk−/pKC215 cells were constructed in substantial accordance with the teaching of Example 4, except that plasmid pKC215, rather than plasmid pKC214, was used in the transformation procedure. The thus constructed Mouse Ltk−/pKC215 transformants were then grown into mass culture.

EXAMPLE 6

Resistance of Transformants to Antibiotics Hygromycin B and G418

The ability of plasmids pKC203, pKC214, and pKC215 to confer resistance to antibiotics hygromycin B and G418 was determined by testing transformed and non-transformed *E. coli* and Mouse Ltk− cells for growth on media with varying amounts of the antibiotics. The media and culture conditions for *E. coli* and Mouse Ltk− cells are substantially as described respectively in Examples 1A and 4. The results of the test are presented below in Tables 1 and 2 wherein '+' indicates growth, '−' indicates no growth, and 'N/T' indicates not tested.

TABLE 1

Resistance to Antibiotic Hygromycin B

| Cell Type | Antibiotic Concentration of Culture Medium | | |
|---|---|---|---|
| | 0 μg./ml. | 200 μg./ml. | 400 μg./ml.* |
| *E. coli* K12 | + | − | − |
| *E. coli* K12 BE827/pKC203 | + | + | + |
| *E. coli* K12 BE827 | + | − | − |
| *E. coli* K12 BE827/pKC214 | N/T | + | N/T |
| *E. coli* K12 BE827/pKC215 | N/T | + | N/T |
| Mouse Ltk− | + | − | N/T |
| Mouse Ltk−/pKC214 | + | + | + |
| Mouse Ltk−/pKC215 | + | + | + |

*Mouse Ltk−/pKC214 and Mouse Ltk−/pKC215 cells not only replicated at 400 μg./ml but also survived higher concentrations exceeding 1000 μg./ml.

TABLE 2

Resistance to Antibiotic G418

| Cell Type | Antibiotic Concentration of Culture Medium | | | |
|---|---|---|---|---|
| | 0 μg/ml | <75 μg/ml | 75 μg/ml | 500 μg/ml |
| *E. coli* K12/pKC203 | + | + | + | N/T |
| Mouse Ltk− | + | + | − | − |
| Mouse Ltk−/pKC214 | + | + | + | + |
| Mouse Ltk−/pKC215 | + | + | + | − |

EXAMPLE 7

Construction of Plasmids pGD1 and pGD2 and Transformants *E. Coli* K12 BE827/pGD1 and *E. coli* K12 BE827/pGD2

Plasmid pLG669, the construction of which is described in Guarente and Ptashne, 1981, Proc. Nat. Acad. Sci. USA 78(4): 2199, contains a unique BamHI restriction site in the cytochrome c gene. Cloning the 7.5 kb BglII fragment of plasmid pKC203 into this site, as described below, allows for the expression of the antibiotic hygromycin B resistance gene. The desired insertion is easily carried out since BglII fragments contain 5' extensions with the sequence GATC that are identical to 5' extensions of BamHI fragments. Therefore BglII fragments and BamHI fragments are compatible and can be ligated directly for the production of recombinants.

Plasmids pGD1 and pGD2 and transformants *E. coli* K12 BE827/pGD1 and *E. coli* K12 BE827/pGD2 are constructed in substantial accordance with the teaching of Example 3, except that plasmid pLG669, with the unique BamHI site, is used instead of plasmid pSV5gpt. Depending upon the orientation of the BglII fragment, plasmids of two orientations result. Plasmid pGD1 designates recombinant plasmids in which the SalI restriction site is closest to the ura gene. Plasmid pGD2 designates plasmids with the reverse orientation.

EXAMPLE 8

Construction of *Saccharomyces cerevisiae*/pGD1

Yeast (*Saccharomyces cerevisiae*) is typically grown in 1% yeast extract/2% bacto-peptone using conventional microbiological procedures well known in the art. The transformation of plasmid pGD1 into yeast is carried out in substantial accordance with the teaching of Hinnen et al., 1978, Proc. Nat. Acad. Sci. USA 75: 1929. Transformants are selected by adding lethal doses of antibiotic hygromycin B to the culture medium.

EXAMPLE 9

Construction of *Saccharomyces cerevisiae*/pGD2

The desired transformants are constructed in substantial accordance with the teaching of Example 8, except that plasmid pGD2 is used instead of plasmid pGD1.

EXAMPLE 10

Construction of Plasmids pGD3 and pGD4 and Transformants *E. coli* K12 BE827/pGD3 and *E. coli* K12 BE827/pGD4

Plasmid p04, the construction of which is described in Solnick, 1981, Cell 24: 135, contains the major Adenovirus 2 (Ad2) late promoter at map coordinates 15.4 (EcoRI) to 16.6 (HindIII). Cloning the 7.5 kb BglII fragment of plasmid pKC203 into the HindIII site of plasmid p04 allows for the expression of the antibiotic hygromycin B resistance gene.

The desired construction is conveniently done by adding, in substantial accordance with the teaching of Ullrich et al., 1977, Science 196: 1313, HindIII linkers* to the 7.5 kb BglII fragment and then ligating the thus modified fragment to HindIII treated plasmid pϕ4 by use of T4 DNA ligase. HindIII restriction and T4 DNA ligase enzyme are respectively available with instructions for use from the firms cited in Examples 2 and 3. After the 7.5 kb BglII fragment is provided with the HindIII linkers, the ligation of the fragment onto plasmid pϕ4 to form plasmids pGD3 and pGD4 is carried out in substantial accordance with the teaching of Example 3. The subsequent transformation into *E. coli* K12 BE827 to form *E. coli* K12 BE827/pGD3 and *E. coli* K12 BE827/pGD4 is also carried out according to the teaching of Example 3.
*HindIII [(d(CCAAGCTTGG)] and other linkers are readily available at:
Collaborative Research Inc.
1365 Main Street
Waltham. MA 02154

As explained in Examples 3 and 7, plasmids of two orientations result depending upon the orientation of the inserted resistance conferring fragment. Plasmid pGD3 designates recombinant plasmids in which the SalI restriction site of the inserted antibiotic hygromycin B conferring fragment is closest to the EcoRI site of the AD2 promoter. Plasmid pGD4 designates plasmids with the reverse orientation.

EXAMPLE 11

Construction of Mouse Ltk−/pGD3

The construction of Mouse Ltk−/pGD3 is carried out in substantial accordance with the teaching of Example 4, except that plasmid pGd3 is used instead of plasmid pKC214.

EXAMPLE 12

Construction of Mouse Ltk−/pGD4

The construction of Mouse Ltk−/pGD4 is carried out in substantial accordance with the teaching of Example 4, except that plasmid pGD4 is used instead of plasmid pKC215.

EXAMPLE 13

Construction of Plasmid pKC222 and Transformant *E. coli* K12 BE827/pKC222

A. Isolation of the 2.7 kb SalI/BglII Fragment of Plasmid pKC203

About 5 μg. of plasmid pKC203 DNA was treated with SalI and BglII restriction enzymes according to the instructions and under the conditions specified by the manufacturer*. A 2.75 kb fragment that contained the genes and control elements for resistance to antibiotics hygromycin B and G418 was recovered by conventional procedures.
*Restriction enzymes and instructions can be obtained from the sources cited in Example 2.

B. Ligation and Final Construction

About 5 μg. of plasmid pKC7 (ATCC No. 37084), the construction of which is disclosed in Rao and Rogers, 1979, Gene 7: 79, were treated with SalI and BglII restriction enzymes. After the enzymes were inactivated by heating at 70° C. for 5 minutes, about 1 μg. of the DNA was mixed in a 1:1 ratio with the 2.75 kb SalI/BglII fragment of pKC203. The fragments were joined using T4 DNA ligase according to the instructions and under the conditions specified by the manufacture as cited in claim 3. The resulting plasmid pKC222 was transformed into *E. coli* K12, in substantial accordance with the teaching of Example 3, and was shown to confer resistance to antibiotics ampicillin, hygromycin B and G418.

EXAMPLE 14

Isolation of the Hygromycin B Resistance Conferring 1.51 kb SacI/BglII Fragment of Plasmid pKC222

The desired DNA fragment was isolated in substantial accordance with the teaching of Example 13A except that SacI, rather than SalI, was used with BglII for the restriction digest.

EXAMPLE 15

Isolation of the G418 Resistance Conferring 1.65 kb EcoRI/SalI Fragment of Plasmid pKC222

The desired DNA fragment was isolated in substantial accordance with the teaching of Example 13A except that EcoRI, rather than BglII, was used with SalI for the restriction digest.

EXAMPLE 16

Construction of Plasmids pGD10 and pGD11 and Transformants E. coli K12 BE827/pGD10 and E. coli K12 BE827/pGD11

The desired plasmids are constructed in substantial accordance with the teaching of Examples 3 and 10 except that the 1.51 kb SacI/BglII fragment of plasmid pKC222 is used instead of the 7.5 kb BglII fragment of plasmid pKC203 and except that BglII, rather than HindIII, linkers are attached to the antibiotic resistance conferring fragment. The 1.51 kb fragment with the BglII linkers is inserted into plasmid pSV5gpt in substantial accordance with the procedure taught in Example 3.

As explained in Examples 3 and 7, plasmids of two orientations result depending upon the orientation of the inserted antibiotic resistance conferring fragment. Plasmid pGD10 designates recombinant plasmids in which the AvaI restriction site of the inserted hygromycin B resistance conferring fragment is closest to the HindIII site of the gpt gene. Plasmid pGD11 designates plasmids with the reverse orientation.

Transformation of plasmids pGD10 and pGD11 into E. coli K12 BE827 to respectively form E. coli K12 BE827/pGD10 and E. coli K12 BE827/pGD11 is also carried out in substantial accordance with the teaching of Example 3.

EXAMPLE 17

Construction of Mouse Ltk−/pGD10

The desired construction is carried out in substantial accordance with the teaching of Example 4 except that plasmid pGD10, rather than plasmid pKC214, is used in the transformation procedure. The thus constructed Mouse Ltk−/pGD10 can be grown into mass culture.

EXAMPLE 18

Construction of Mouse Ltk−/pGD11

The desired construction is carried out in substantial accordance with the teaching of Example 4 except that plasmid pGD11, rather than plasmid pKC214, is used in the transformation procedure. The thus constructed Mouse Ltk−/pGD11 can be grown into mass culture.

EXAMPLE 19

Construction of Plasmids pGD12 and pGD13 and Transformants E. coli K12 BE827/pGD12 and E. coli K12 BE827/pGD13

The desired plasmids are constructed in substantial accordance with the teaching of Examples 3 and 10 except that the 1.65 kb EcoRI/SalI fragment of plasmid pKC222 is used instead of the 7.5 kb BglII fragment of plasmid pKC203 and except that BglII, rather than HindIII, linkers are attached to the antibiotic resistance conferring fragment. The 1.65 kb fragment with BglII linkers is inserted into plasmid pSV5gpt in substantial accordance with the procedure taught in Example 3.

As explained in Example 16, plasmids of two orientations result. Plasmid pGD12 designates recombinant plasmids in which the PstI restriction site of the inserted antibiotic G418 resistance conferring fragment is closest to the HindIII site of the gpt gene. Plasmid pGD13 designates plasmids with the reverse orientation.

Transformation of plasmids pGD12 and pGD13 into E. coli K12 BE827 to respectively form E. coli K12 BE827/pGD12 and E. coli K12 BE827/pGD13 is also carried out in substantial accordance with the teaching of Example 3 except that antibiotic G418, rather than hygromycin B, is used for selection of transformants.

EXAMPLE 20

Construction of Mouse Ltk−/pGD12

The desired construction is carried out in substantial accordance with the teaching of Example 4 except that plasmid pGD12, rather than plasmid pKC214, is used in the transformation procedure and except that antibiotic G418, rather than hygromycin B, is used for selecting transformants. The thus constructed Mouse Ltk−/pGD12 can be grown into mass culture.

EXAMPLE 21

Construction of Mouse Ltk−/pGD13

The desired construction is carried out in substantial accordance with the teaching of Example 4 except that plasmid pGD13, rather than plasmid pKC214, is used in the transformation procedure and except that antibiotic G418, rather than hygromycin B, is used for selecting transformants. The thus constructed Mouse Ltk−/pGD13 can be grown into mass culture.

EXAMPLE 22

Construction of Plasmids pGD14 and pGD15 and Transformants E. coli K12 BE827/pGD14 and E. coli K12 BE827/pGD15

The 2.75 kb SalI/BGlII fragment of plasmid pKC203 was isolated following the procedure described in Example 13. Molecular linkers are then attached according to the teaching of Example 10 except that BglII, rather than HindIII, linkers are used. The resulting fragment is then inserted into plasmid pSV5gpt, in substantial accordance with the procedure taught in Example 3, to form the desired plasmids.

As explained in Example 16, plasmids of two orientations result. Plasmid pGD14 designates recombinant plasmids in which the AvaI restriction site of the antibiotic conferring fragment is closest to the HindIII site of the gpt gene. Plasmid pGD15 designates plasmids with the reverse orientation.

Transformation of plasmids pGD14 and pGD15 into E. coli K12 BE827 to respectively form E. coli K12 BE827/pGD14 and E. coli K12 BE827/pGD15 is also carried out in substantial accordance with the teaching of Example 3.

EXAMPLE 23

Construction of Mouse Ltk−/pGD14

The desired construction is carried out in substantial accordance with the teaching of Example 4 except that plasmid pGD14, rather than plasmid pKC214, is used in the transformation procedure. The thus constructed Mouse Ltk−/pGD14 can be grown into mass culture.

EXAMPLE 24

Construction of Mouse Ltk−/pGD15

The desired construction is carried out in substantial accordance with the teaching of Example 4 except that plasmid pGD15, rather than plasmid pKC214, is used in the transformation procedure. The thus constructed Mouse Ltk−/pGD14 can be grown into mass culture.

EXAMPLE 25

Construction of Plasmid pSC701 and Transformant E. coli K12 BE827/pSC701

About 5 µl. (5 µg.) of plasmid pKC203 (isolated in Example 1) in TE buffer (10 mM Tris-HCl, pH 8.0, 1 mM EDTA), 5 µl. DTT (100 mM Dithiothreitol), 5 µl. (1000 mg./ml.) BSA (bovine serum albumin), 25 µl. water, 5 µl. (5 units) BglII restriction enzyme, and 5 µl. 10X reaction mix* were incubated at 37° C. for about 1 hour. The reaction was terminated by incubation at 70° C. for 5 minutes and then the reaction mixture was cooled on ice, extracted with each of phenol and chloroform:isoamyl alcohol (24:1), and then ethanol precipitated. The resultant BglII restriction fragments were dissolved in 5 µl. of 5 mM NaCl and then ligated. Ligation was carried out by reacting 1 µl. of the BglII restricted DNA with about 38 µl. water, 5 µl. (10 mM) ATP, 5 µl. ligation mix**, and 1 µl. T4 DNA ligase (~$10^5$ New England Bio Lab Units) at 16° C. for about 16 hours. The reaction was terminated by incubation at 70° C. for 5 minutes. After cooling on ice, the resultant ligated mixture is used to transform E. coli K12 BE827, in substantial accordance with the transformation procedure of Wensink, 1974, on TY plates containing 200 mg./ml. of antibiotic hygromycin B. Some of the transformants, as conventionally shown by gel electrophoresis (Rao and Rogers, 1978) and other tests, contain only the desired ~7.3 kb plasmid. Such a transformant, designated herein as E. coli K12 BE827/pSC701, is selected, plated on TY agar containing 200 µg./ml. of antibiotic hygromycin B, and then cultured using conventional microbiological techniques. The resultant cells are used to isolate plasmid pSC701 according to the procedure of Example 1A. The presence of the antibiotic hygromycin B and G418 resistance genes in plasmid pSC701 was further confirmed by subsequent transformation, selection, and restriction enzyme analysis. A restriction site and functional map of plasmid pSC701 is shown in FIG. 6 of the accompanying drawings.

*Reaction mix (10X) for BglII restriction enzyme was prepared with the following composition: 600 mM NaCl, 100 mM Tris-HCl, pH 7.4, 100 mM MgCl$_2$.
**Ligation mix was prepared with the following composition:
500 mM Tris-HCl, pH 7.8, 200 mM Dithiothreitol,
100 mM MgCl$_2$.

EXAMPLE 26

Construction of Plasmids pKC257 and pKC259 and Transformants E. coli K12 BE783/pKC257 and E. coli K12 BE783/pKC259

The desired plasmid was made in substantial accordance with the teaching of Example 25 except that plasmid pSC701 and HaeII restriction enzyme and reaction mix*, rather than plasmid pKC203 and BglII restriction enzyme and reaction mix, were used. Plasmid pSC701 contains more than one HaeII restriction site so therefore HaeII digestion and subsequent ligation results in a mixture of different plasmids.

*Reaction mix (10X) for HaeII restriction enzyme was prepared with the following composition: 60 mM Tris-HCl, pH 7.4, 60 mM MgCl$_2$.

The resultant ligated mixture, which includes the desired hygromycin B resistance-conferring ~4.2 kb plasmid pKC257 and also the hygromycin B, G418, and apramycin resistance-conferring ~5.0 kb plasmid pKC259, was used to transform E. coli K12 BE783 (deposited and made part of the permanent stock culture collection of the Northern Regional Research Laboratory, Peoria, Ill. under the accession number B-15020), in substantial accordance with the transformation procedure of Example 25. The desired transformants were selected, plated on TY agar containing 200 µg./ml. of antibiotic hygromycin B, and then cultured separately using conventional microbiological techniques. Transformants containing pKC257 were easily and conventionally identified by screening for hygromycin B resistance and transformants containing plasmid pKC259 were identified by screening for apramycin and hygromycin B resistance. The transformants, designated herein as E. coli K12 BE783/pKC257 and E. coli k12 BE783/pKC259, were respectively used to isolate plasmids pKC257 and pKC259 according to the procedure of Example 1A. The presence of the antibiotic resistance genes in the respective plasmids was further confirmed by subsequent transformation, selection, and restriction enzyme analysis. A restriction site and functional map of each of plasmids pKC257 and pKC 259 is shown respectively in FIGS. 6 and 7 of the accompanying drawings.

EXAMPLE 27

Construction of Plasmid pKC261 and Transformant E. coli K12 BE783/pKC261

The desired plasmid was made in substantial accordance with the teaching of Example 25 except that plasmid pKC257 and Sau3 AI restriction enzyme and reaction mix*, rather than plasmid pSC701 and BglII restriction enzyme and reaction mix, were used. The desired plasmid pKC261 is ~3.2 kb and confers resistance to hygromycin B.

Reaction mix (10X) for Sau 3AI restriction enzyme was prepared with the following composition.
500 mM NaCl,
60 mM Tris-HCl, pH 7.5,
50 mM MgCl$_2$.

The resultant ligated mixture is used to transform E. coli K12 BE783 in substantial accordance with the transformation procedure of Example 25. Transformants, designated herein as E. coli K12 BE783/pKC261, are selected and used to isolate plasmid pKC261 according to the procedure of Example 1A. The presence of the antibiotic hygromycin B resistance gene in plasmid pKC261 was further confirmed by subsequent transformation, selection, and DNA sequence analysis. A restriction site and functional map of plasmid pKC261 is shown in FIG. 7 of the accompanying drawings.

EXAMPLE 28

Construction of Plasmid pKC275 and Transformant E. Coli K12 BE1041/pKC275

A. Partial HaeII Digestion of Plasmid pKC261

About 5 µl. (5 µg.) of plasmid pKC261 (isolated in Example 27) in TE buffer, 5 µl DTT, 5 µl. (1000 mg./ml.) BSA, 25 µl. water, 5 µl. (5 units) HaeII restriction enzyme, and 5 µl. 10X reaction mix were incubated at 37° C. for about 1 hour. After the reaction was terminated by incubation at 70° C. for 5 minutes, the reaction mixture was cooled on ice, extracted with each of phenol and chloroform:isoamyl alcohol (24:1), and then ethanol precipitated. The resultant HaeII restriction fragments were dissolved in 5 µl. of 5 mM NaCl.

B. Isolation of ~394 nt plac Fragment Containing HaeII Termini

About 5 µl. (5 µg.) of plasmid pUR222 (isolated from *E. coli* K12 BE1166/pUR222 in substantial accordance with the teaching of Example 1) in TE buffer was HaeII digested in substantial accordance with the teaching of Example 28A except that the reaction mixture was incubated at 37° C. for about 2 hours to insure that the digestion was complete and not partial. The resultant HaeII restriction fragments were dissolved in 5 µl. of 5 mM NaCl.

*E. coli* K12 BE1166/pUR222 is a strain deposited and made part of the permanent stock culture collection, Northern Regional Research Laboratory, Peoria, Ill. It is available to the public as a preferred source and stock reservoir of plasmid pUR222 under the accession number B-15023.

C. Ligation and Transformation

About 4 µl. each of plasmid pKC261 and plasmid pUR222 HaeII restriction fragments (respectively prepared in Examples 28A and B), 31 µl. water, 5 µl. (10 mM) ATP, 5 µl. ligation mix, and 1 µl. T4 DNA ligase (~$10^5$ New England Bio Lab Units) were reacted at 16° C. for about 16 hours. After the reaction was terminated by incubation at 70° C. for 5 minutes, the resultant ligated mixture was cooled on ice. The DNA was then transformed into *E. coli* K12 BE1041 (deposited and made part of the permanent stock culture collection of the Northern Regional Research Laboratory, Peoria, Ill. under the accession number B-15021), in substantial accordance with the transformation procedure of Example 25. Transformants containing only the desired ~3.6 kb plasmid pKC275 were designated as *E. coli* K12 BE1041/pKC275. Such a transformant was selected, plated, cultured, and used for subsequent plasmid isolations. Both the presence of the ~394 nt plac-containing fragment and the detailed structure of plasmid pKC275 were conventionally determined by gel electrophoretic and restriction enzyme analysis.

Because plasmid pKC261 has three HaeII restriction sites, a partial HaeII digestion results in a mixture of different HaeII fragments. Consequently, the above illustrative procedure results in the construction of both plasmid pKC275 and also the various insertional isomers of plasmid pKC275. Recombinant plasmids of two orientations are also produced since the ~394 nt plac-containing fragment can be ligated in either direction. Those skilled in the art will understand that the variously oriented plasmid isomers and also the resultant transformants can be readily isolated and identified by conventional means. A restriction site and functional map of plasmid pKC275 is presented in FIG. 8 of the accompanying drawings.

EXAMPLE 29

Construction of Plasmid pKD264 and Transformant *E. Coli* K12 BE783/pKC264

A. EcoRI Digestion of Plasmid pKC259

The desired digestion was carried out in substantial accordance with the teaching of Example 28B except that plasmid pKC259 and EcoRI restriction enzyme and reaction mix*, rather than plasmid pUR222 and HaeII restriction enzyme and reaction mix, were used. The resultant EcoRI restriction fragments were dissolved in 5 µl. of 5 mM NaCl.

*Reaction mix (10X) for EcoRI restriction enzyme was prepared with the following composition:
500 mM NaCl,
1000 mM Tris-HCl, pH 7.5,
50 mM MgCl$_2$.

B. EcoRI Digestion of Plasmid YEp24 For Subsequent Isolation of 2µ DNA

Plasmid YEp24 was isolated from *E. coli* K12 BE1139/YEp24 in substantial accordance with the teaching of Example 1. *E. coli* K12 BE1139/YEp24 is a strain deposited and made part of the permanent stock culture collection of the Northern Regional Research Laboratory, Peoria, Illinois. It is available to the public as a preferred source and stock reservoir of the plasmid under the accession number B-15022. The desired EcoRI digestion of plasmid YEp24 was carried out in substantial accordance with the teaching of Example 29A and the resultant EcoRI restriction fragments were dissolved in 5 µl. of 5 mM NaCl.

C. Ligation and Transformation

The EcoRI digested plasmid pKC259 and plasmid YEp24 (respectively prepared in Examples 29A and B) were ligated and subsequently transformed into *E. coli* K12 BE783 in substantial accordance with the teaching of Example 28C. Transformants containing only the desired ~7.2 kb hygromycin B, apramycin, and G418 resistance-conferring plasmid are designated as *E. coli* K12 BE783/pKC264. Such a transformant is conventionally selected, plated, cultured, and used for subsequent plasmid isolations.

Those skilled in the art will recognize that the 2µ DNA can be ligated in either direction and that therefore plasmid pKC$_{264}$ and also plasmids with the reverse orientation result from the above procedure. The various plasmids and resultant transformants can be readily isolated and identified by conventional means. A restriction site and functional map of plasmid pKC264 is presented in FIG. 8 of the accompanying drawings.

EXAMPLE 30

Construction of Plasmids pLO314 and pLO315 and Transformants *E. coli* K12 BE783/pLO314 and *E. coli* K12 BE783/pLO315

A. BglII Digestion of Plasmid pKC259

The desired digestion is carried out in substantial accordance with the teaching of Example 28B except that plasmid pKC259 and BglII restriction enzyme and reaction mix, rather than plasmid pUR222 and HaeII restriction enzyme and reaction mix, is used. The resultant BglII digest is dissolved in 5 mM NaCl.

B. BglII Digestion of Plasmid pSV5gpt

The desired digestion was carried out in substantial accordance with the teaching of Example 28B except that plasmid pSV5gpt and BglII restriction enzyme and reaction mix, rather than plasmid pUR222 and HaeII restriction enzyme and reaction mix, was used. The resultant BglII digest is dissolved in 5 mM NaCl.

C. Ligation and Transformation

The desired ligation is carried out in substantial accordance with the teaching of Example 28C except that BglII digested plasmids pKC259 and pSV5gpt, rather than plasmids pKC261 and pUR222, are used. The resultant ligated mixture is used to transform *E. coli* K12 BE783 in substantial accordance with the transformation procedure of Wensink, 1974, on TY plates containing 200 μg./ml. of antibiotic hygromycin B. Some of the transformants, as can be conventionally shown by gel electrophoresis (Rao and Rogers, 1978) and other tests, contain only the desired plasmid pLO314 or the desired plasmid pLO315. Such transformants are selected, plated, cultured and constitute the desired *E. coli* K12 BE783/pLO314 and *E. coli* K12 BE783/pLO315 transformants. The transformants are used for subsequent isolation of the desired plasmids pLO314 and pLO315.

Figure 9:
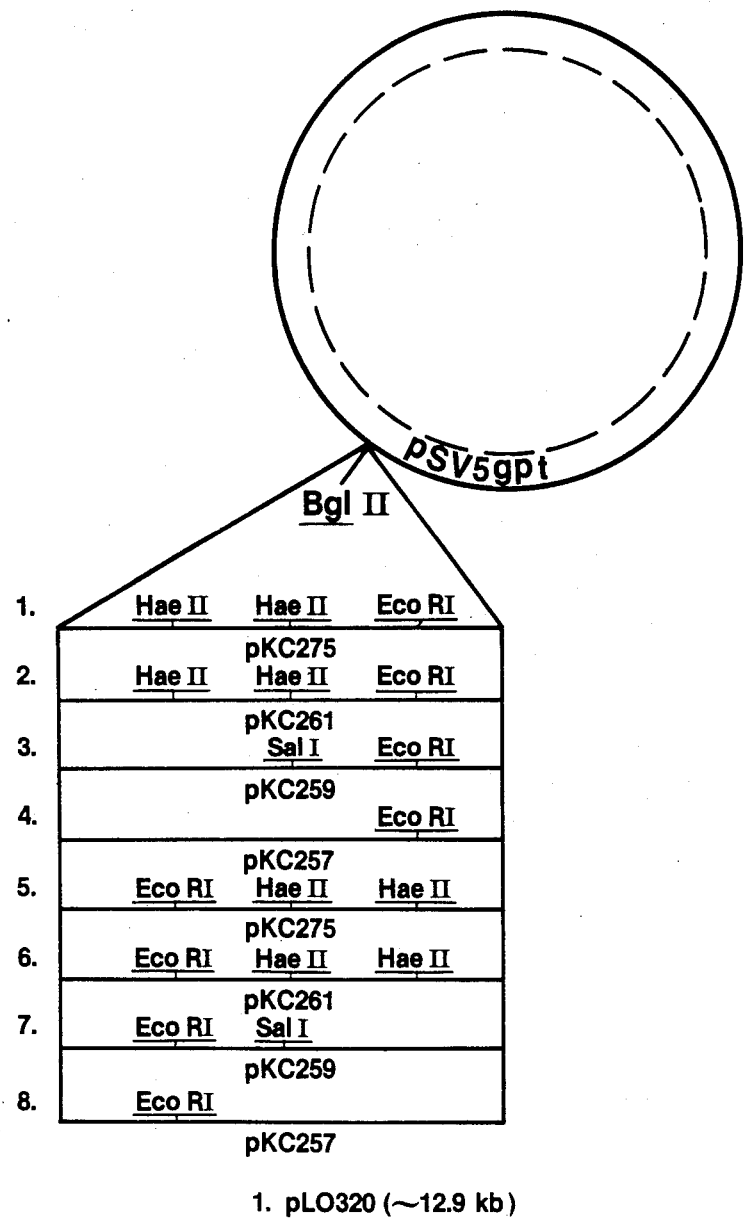
FIG. 9. The restriction site and functional map of plasmids pLO314–pLO321.

Recombinant plasmids of two orientations result because the DNA fragments are ligated in either direction. Those skilled in the art will understand that the desired plasmids are readily distinguished and identified by the conventional techniques of restriction enzyme and electrophoresis analysis. A restriction site and functional map of each of plasmids pLO314 and pLO315 is presented in FIG. 9 of the accompanying drawings.

EXAMPLE 31

Construction of Mouse Ltk−/pLO314

The desired construction is made in substantial accordance with the teaching of Example 4 except that plasmid pLO314, rather than pKC214, is used. The thus constructed Mouse Ltk−/pLO314 transformants are then grown into mass culture.

EXAMPLE 32

Construction of Mouse Ltk−/pLO315

The desired construction is made in substantial accordance with the teaching of Example 4 except that plasmid pLO315, rather than pKC214, is used. The thus constructed Mouse Ltk−/pLO315 transformants are then grown into mass culture.

EXAMPLE 33

Construction of pLO316 and pLO317 and Transformants *E. coli* K12 BE783/pLO316 and *E. coli* K12 BE783/pLO317

A. SacI Digestion of Plasmid pKC257 and Addition of BglII Linkers

The desired digestion is carried out in substantial accordance with the teaching of Example 28B except that plasmid pKC257 and SacI restriction enzyme and reaction mix*, rather than plasmid pUR222 and HaeII restriction enzyme and reaction mix, are used.
*Reaction mix (10X) for SacI restriction enzyme is prepared with the following composition:
600 mM NaCl,
100 mM Tris-HCl, pH 7.4,
100 mM MgCl$_2$.

The addition of BglII linkers** to the SacI digested plasmid pKC257 termini is carried out in substantial accordance with the teaching of St. John et al., 1981, J. Mol. Biol. 152:317.
**BglII [(d(CAGATCTG)] and other linkers are readily available at:
Collaborative Research Inc.
1365 Main Street
Waltham, MA 02154

B. Ligation And Transformation

Linear plasmid pKC257 with BglII termini is ligated to BglII digested plasmid pSV5gpt (prepared in Example 30B) in substantial accordance with the teaching of Example 30C. The ligated mixture is used to transform *E. coli* K12 BE783 in the manner also disclosed in Example 30C. The resultant *E. coli* K12 BE783/pLO316 and *E. coli* K12 BE783/pLO317 transformants are used for isolation of the desired plasmids pLO316 and pLO317. As explained in Example 30C, plasmids of two orientations result depending upon the orientation of the inserted resistance-conferring fragment. The plasmids and resultant transformant can be readily distinguished and identified by conventional means. A restriction site and functional map of each of plasmids pLO316 and pLO317 is presented in FIG. 9 of the accompanying drawings.

EXAMPLE 34

Construction of Mouse Ltk−/pLO316 and Mouse Ltk−/pLO317

The desired constructions are separately made in substantial accordance with the teaching of Example 4 except that either of plasmids pLO316 or pLO317, rather than plasmid pKC214, is used. The thus constructed Mouse Ltk−/pLO316 and Mouse Ltk−/pLO317 transformants are then separately grown into mass culture.

EXAMPLE 35

Construction of Plasmids pLO318 and pLO319 and Transformants *E. coli* K12 BE783/pLO318 and *E. coli* K12 BE783/pLO319

The desired constructions are made in substantial accordance with the teaching of Example 33 except that plasmid pKC261, rather than plasmid pKC257, is used. The resultant *E. coli* K12 BE783/pLO318 and *E. coli* K12 BE783/pLO319 transformants are used for isolation of the desired plasmids pLO318 and pLO319. As explained in Example 30C, plasmids of two orientations result depending upon the orientation of the inserted resistance-conferring fragment. The plasmids and resultant transformants can be readily distinguished and identified by conventional means. A restriction site and functional map of each of plasmids pLO318 and pLO319 is presented in FIG. 9 of the accompanying drawings.

EXAMPLE 26

Construction of Mouse Ltk−/pLO318 and Mouse Ltk−/pLO319

The desired constructions are separately made in substantial accordance with the teaching of Example 4 except that either of plasmids pLO318 or pLO319, rather than plasmid pKC214, is used. The thus constructed Mouse Ltk−/pLO318 and Mouse Ltk−/pLO319 transformants are then separately grown into mass culture.

EXAMPLE 37

Construction of Plasmids pLO320 and pLO321 and Transformants *E. coli* K12 BE1041/pLO320 and *E. coli* K12 BE1041/pLO321

The desired constructions are made in substantial accordance with the teaching of Example 33 except that plasmid pKC275, rather than plasmid pKC257, is used. The resultant *E. coli* K12 BE1041/pLO320 and *E. coli* K12 BE1041/pLO321 transformants are used for isolation of the desired plasmids pLO320 and pLO321. As explained in Example 30C, plasmids of two orientations result depending upon the orientation of the inserted resistance-conferring fragment. The plasmids and resultant transformants can be readily distinguished and identified by conventional means. A restriction site and functional map of each of plasmids pLO320 and pLO321 is presented in FIG. 9 of the accompanying drawings.

EXAMPLE 38

Construction of Mouse Ltk−/pLO320 and Mouse Ltk−/pLO321

The desired constructions are separately made in substantial accordance with the teaching of Example 4 except that either of plasmids pLO320 or pLO321, rather than plasmid pKC214, is used. The thus constructed Mouse Ltk−/pLO320 and Mouse Ltk−/pLO321 transformants are then separately grown into mass culture.

EXAMPLE 39

Construction of Plasmid pKC273 and Transformant *E. coli* K12 BE783/pKC273

A. Construction of a 2μ and ura+ Gene-Containing Linear DNA With BamHI and SalI Termini About 5 μl. (5 μg.) of plasmid pYEp24 in TE buffer, 5 μl. DTT, 5 μl. (1000 mg./ml.) BSA, 25 μl. water, 5 μl. (5 units) BamHI restriction enzyme, and 5 μl. 10X reaction mix* were incubated at 37° C. for 1 hour and then at 70° C. for 5 minutes. The BamHI digested DNA was cooled on ice, ethanol precipitated, and then dissolved in 30 μl. of water to which 5 μl. of 10X SalI buffer (reaction mix)* and 5 μl. DTT, 5 μl. (1000 mg./ml.) BSA, and 5 μl. (5 units) SalI restriction enzyme were added. The resultant mixture was incubated at 37° C. for 1 hour, than at 70° C. for 5 minutes, and finally cooled to 4° C. The mixture was then extracted with each of phenol and chloroform:isoamyl alcohol (24:1) and lastly ethanol precipitated. The resultant precipitate contained the desired linear DNA and was dissolved in 5 μl. of 5 mM NaCl and stored at 4° C. for future use.
*Reaction mix (10X) for BamHI and SalI restriction enzymes were each prepared with the following composition:
1500 mM NaCl,
60 mM Tris-HCl, pH 7.9,
60 mM MgCl$_2$.

B. Construction of a Hygromycin B Resistance Gene-Containing Linear DNA with BamHI and SalI Termini The desired linear DNA was constructed in substantial accordance with the teaching of Example 39A except that plasmid pKC259, rather than plasmid YEp24, was used. The resultant precipitate contained the desired linear DNA and was dissolved in 5 μl. of 5 mM NaCl and stored at 4° C. for future use.

C. Ligation and Transformation

The desired ligation and transformation into *E. coli* K12 BE783 were carried out in substantial accordance with the teaching of Example 28C except that the DNA fragments prepared in Examples 39A and B, rather than the HaeII fragments of plasmids pUR222 and pKC261, were ligated and used in subsequent transformations. Some of the resultant transformants, as conventionally shown by selection, gel electrophoresis (Rao and Rogers, 1978) and other tests, contained the desired plasmid. Such a transformant, designated as *E. coli* K12 BE783/pKC273, was selected, plated, cultured, and used for subsequent isolation of plasmid pKC273. A restriction site and functional map of plasmid pKC273 is presented in FIG. 10 of the accompanying drawings.

EXAMPLE 40

Construction of *Saccharomyces cerevisiae*/pKC273

Yeast (*Saccharomyces cerevisiae*) was grown in 1% yeast extract/2% bacto-peptone/1% glucose using conventional and known microbiological procedures. The transformation of plasmid pKC273 into yeast was carried out in substantial accordance with the teaching of Hinnen et al., 1978, Proc. Nat. Acad. Sci. USA 75: 1929. Transformants were selected by their ability to grow on minimal media lacking uracil (Ura+ phenotype). Ura+ transformants were subsequently tested for their ability to grow on complex media supplemented with 200 μg./ml. of hygromycin B. Such a dose is lethal to non-transformed cells. *Saccharomyces cerevisiae*/pKC273 transformant cells grow on these media while untransformed *Saccharomyces cerevisiae* are killed.

EXAMPLE 41

Construction of Plasmid pLO378 And Transformant *E. coli* K12 BE783/pLO378

A. PstI Digestion of Plasmid pBR322

The desired digestion is carried out in substantial accordance with the teaching of Example 28B except that plasmid pBR322 and PstI restriction enzyme and reaction mix*, rather than plasmid pUR222 and HaeII restriction enzyme and reaction mix, is used. The resultant PstI digest is dissolved in 5 μl. of 5 mM NaCl.
*Reaction mix (10X) for PstI restriction enzyme was prepared with the following composition:
500 mM NaCL,
60 mM Tris-HCl, pH 7.4,
60 mM MgCl$_2$.

B. PstI Digestion of Plasmid pKC264

The desired digestion was carried out in substantial accordance with the teaching of Example 41A except that plasmid pKC264, rather than plasmid pBR322, was used. The resultant PstI digest was dissolved in 5 μl. of 5 mM NaCl.

C. Ligation and Transformation

The desired ligation and transformation into *E. coli* K12 BE783 is carried out in substantial accordance with the teaching of Example 28C except that the DNA fragments prepared in Examples 41A and B, rather than the HaeII fragments of plasmids pUR222 and pKC261, are ligated and used in subsequent transformations. Some of the transformants, as can be conventionally shown by antibiotics selection, gel electrophoresis (Rao and Rogers, 1978) and other tests, contain the desired plasmid. Such a transformant, designated as *E. coli* K12 BE783/pLO378, is selected, plated, cultured and used for subsequent isolation of plasmid pLO378.

As explained in Example 30C, plasmids of two orientations result depending upon the orientation of the inserted resistance-conferring fragment. Therefore, in addition to plasmid pLO378, the above procedure also generates plasmids with the reverse orientation. Those skilled in the art can readily distinguish and identify these plasmids and resultant transformants by conventional means. A restriction site and functional map of plasmid pLO378 is presented in FIG. 10 of the accompanying drawings.

EXAMPLE 42

Construction of *Saccharomyces cerevisiae*/pLO378

The desired transformation is carried out in substantial accordance with the teaching of Example 40 except that the G418 resistance gene-containing plasmid pLO378, rather than plasmid pKC273, is used. Transformants are identified by conventionally screening the recipient yeast cells for the presence of plasmid DNA. The desired *Saccharomyces cerevisiae*/pLO378 transformants are thus readily identified and isolated.

We claim:

1. A recombinant DNA cloning vector comprising:
   (a) a eukaryotic promoter,
   (b) one or two different structural genes and associated control elements that convey resistance to either or both antibiotics hygromycin B and G418 when transformed into a host cell that is sensitive to either or both antibiotics for which resistance is conveyed, said host cell being susceptible to transformation, cell division, and culture, and
   (c) a prokaryotic replicon, said replicon being functional when said host cell is prokaryotic,
subject to the limitations that the one or two structural genes and associated control elements are adjacent to and, in a eukaryotic host cell, transcribed from the eukaryotic promoter, that a single gene and associated control element conveys resistance to only either one of hygromycin B or G418, and that the gene conveying resistance to G418 does not code for the enzyme phosphotransferase.

2. A recombinant DNA cloning vector comprising:
   (a) a eukaryotic promoter,
   (b) the 7.5 kb BglII restriction fragment of plasmid pKC203, and
   (c) a prokaryotic replicon, said replicon being functional when said vector is transformed into a prokaryotic host cell,
subject to the limitations that
(1) said 7.5 kb BglII restriction fragment is adjacent to the eukaryotic promoter, and
(2) that any antibiotic resistance-conferring gene contained within said 7.5 kb BglII restriction fragment is, in a eukaryotic host cell, transcribed from the eukaryotic promoter.

3. The recombinant DNA cloning vector of claim 2 which is a plasmid and wherein the prokaryotic replicon is selected from the group consisting of the pBR322 replicon, pMB1, NR1, RK2, R6K, pSC101, RP1, RP4, RSF1010, pUB110, and SLP1.2 and the eukaryotic promoter is independently selected from the group consisting of the SV40 early promoter, SV40 late promoter, HSVITK promoter, adenovirus promoter, Ad 2 promoter, polyoma promoter, mouse sarcoma virus promoter, yeast trp-1 promoter, yeast leu 2 promoter, yeast his 3 promoter, and the yeast cytochrome c promoter.

4. The recombinant DNA cloning vector of claim 3 wherein the prokaryotic replicon is the pBR322 replicon and the eukaryotic promoter is the SV40 early promoter.

5. The recombinant DNA cloning vector of claim 3 wherein the prokaryotic replicon is the pBR322 replicon and the eukaryotic promoter is the SV40 late promoter.

6. The recombinant DNA cloning vector of claim 3 wherein the prokaryotic replicon is the pBR322 replicon and the eukaryotic promoter is the HSVITK promoter.

7. The recombinant DNA cloning vector of claim 3 wherein the prokaryotic replicon is the pBR322 replicon and the eukaryotic promoter is the adenvirus promoter.

8. The recombinant DNA cloning vector of claim 3 wherein the prokaryotic replicon is the pBR322 replicon and the eukaryotic promoter is the polyoma promoter.

9. The recombinant DNA cloning vector of claim 3 wherein the prokaryotic replicon is the pBR322 replicon and the eukaryotic promoter is the mouse sarcoma virus promoter.

10. The recombinant DNA cloning vector of claim 3 wherein the prokaryotic replicon is the pBR322 replicon and the eukaryotic promoter is the yeast trp-1 promoter.

11. The recombinant DNA cloning vector of claim 3 wherein the prokaryotic replicon is the pBR322 replicon and the eukaryotic promoter is the yeast leu 2 promoter.

12. The recombinant DNA cloning vector of claim 3 wherein the prokaryotic replicon is the pBR322 replicon and the eukaryotic promoter is the yeast his 3 promoter.

13. The recombinant DNA cloning vector of claim 3 wherein the prokaryotic replicon is the pBR322 replicon and the eukaryotic promoter is the Ad 2 promoter.

14. The recombinant DNA cloning vector of claim 3 wherein the prokaryotic replicon is the pBR322 replicon and the eukaryotic promoter is the yeast cytochrome c promoter.

15. The recombinant DNA cloning vector of claim 1 which is a plasmid and wherein the genes and associated control elements confer resistance to both hygromycin B and G418 and comprise the 2.75 kg BglII/SalI restriction fragment of plasmid pKC203.

16. The recombinant DNA cloning vector of claim 1 which is a plasmid and wherein the number of said structural genes and associated control elements is limited to one.

17. The plasmid of claim 16 wherein the gene and associated control element confers resistance to hygromycin C and comprises the 1.51 kb SacI/BglII restriction fragment of plasmid pKC222.

18. The plasmid of claim 16 wherein the gene and associated control element confers resistance to G418 and comprises the 1.65 kb EcoRI/SalI restriction fragment of plasmid pKC222.

19. The plasmid of claim 16 wherein the prokaryotic replicon is selected from the group consisting of the pBR322 replicon, pMB1, NR1, RK2, R6K, pSC101, RP1, RP4, RSF1010, pUB110, and SLP1.2 and the eukaryotic promoter is independently selected from the group consisting of the SV40 early promoter, SV40 late promoter, HSVITK promoter, adenovirus promoter, Ad 2 promoter, polyoma promoter, mouse sarcoma virus promoter, yeast trp-1 promoter, yeast leu 2 promoter, yeast his 3 promoter, and the yeast cytochrome c promoter.

20. A plasmid selected from the group consisting of plasmid pKC203, pKC222, pKC214, pKC215, pGD10, pGD11, pGD12, pGD13, pGD14, and pGD15.

21. The plasmid of claim 20 which is plasmid pKC203.

22. The plasmid of claim 20 which is plasmid pKC222.

23. The plasmid of claim 20 which is plasmid pKC214.

24. The plasmid of claim 20 which is plasmid pKC215.

25. The plasmid of claim 20 which is selected from the group consisting of plasmid pGD10, pGD11, pGD12, pGD13, pGD14, and pGD15.

26. A restriction fragment selected from the group consisting of the 7.5kb BglII restriction fragment of plasmid pKC203, the 2.75kb BglII/SalI restriction fragment of plasmid pKC203, the 1.5kb SacI/BglII restriction fragment of plasmid pKC222, and the 1.65kb EcoRI/SalI restriction fragment of plasmid pKC222.

27. The restriction fragment of claim 26 which is the 7.5kb BglII restriction fragment of plasmid pKC203.

28. The restriction fragment of claim 26 which is the 2.75kb BglII/SalI restriction fragment of plasmid pKC203.

29. The restriction fragment of claim 26 which is the 151kb SacI/BglII restriction fragment of plasmid pKC222.

30. The restriction fragment of claim 26 which is the 1.65kb EcoRI/SalI restriction fragment of plasmid pKC222.

31. A transformed host cell comprising a recombinant DNA cloning vector of claim 1.

32. A transformed host cell comprising a recombinant DNA cloning vector of claim 2.

33. The transformed host cell of claim 32 wherein the recombinant DNA cloning vector is a plasmid and wherein the prokaryotic replicon is selected from the group consisting of the pBR322 replicon, pMB1, NR1, RK2, RP4, RSF1010, pUB110, and SLP1.2 and wherein the eukaryotic promoter is independently selected from the group consisting of the SV40 early promoter, HSVITK promoter, adenovirus promoter, Ad 2 promoter, polyoma promoter, mouse sarcoma virus promoter, yeast trp-1 promoter, yeast leu 2 promoter, yeast his 3 promoter, and the yeast cytochrome c promoter.

34. The transformed host cell of claim 33 which is a prokaryotic cell.

35. The transformed host cell of claim 33 which is a eukaryotic cell.

36. The transformed host cell of claim 33 which is selected from the group consisting of *E. coli, E. coli* K12, *E. coli* K12 BE827, Bacillus, *Bacillus subtilis*, and Streptomyces.

37. The transformed host cell of claim 36 which is *E. coli*.

38. The transformed host cell of claim 36 which is *Bacillus subtilis*.

39. The transformed host cell of claim 36 which is Streptomyces.

40. The transformed host cell of claim 32 which is a fungus.

41. The transformed host cell of claim 40 which is selected from the group consisting of Neurospora, Cephalosporium, Aspergillus, Penicillium, and yeast.

42. The transformed host cell of claim 41 which is Neurospora.

43. The transformed host cell of claim 41 which is Cephalosporium.

44. The transformed host cell of claim 41 which is yeast.

45. The transformed host cell of claim 35 which is a mammalian cell.

46. The transformed host cell of claim 45 which is a human cell.

47. The transformed host cell of claim 32 which is a plant cell.

48. The transformed host cell of claim 47 which is an algal cell.

49. A transformed host cell comprising a cloning vector of claim 15.

50. A transformed host cell comprising a cloning vector of claim 16.

51. A transformed host cell selected from the group consisting of Mouse Ltk−/pKC214, Mouse Ltk−/pKC215, *E. coli* K12/pKC214, *E. coli* K12/pKC215, *E. coli* K12 BE827/pKC214, *E. coli* K12 BE827/pKC215, human/pKC214 cell, and mammalian/pKC214 cell.

52. The transformed host cell of claim 51 which is *E. coli* K12/pKC214.

53. The transformed host cell of claim 51 which is *E. coli* K12/pKC215.

54. The transformed host cell of claim 51 which is Mouse Ltk−/pKC214.

55. The transformed host cell of claim 51 which is Mouse Ltk−/pKC215.

56. The transformed host cell of claim 51 which is *E. coli* K12 BE827/pKC214.

57. The transformed host cell of claim 51 which is *E. coli* K12 BE827/pKC215.

58. The transformed host cell of claim 51 which is a human/pKC214 cell.

59. A transformed host cell selected from the group consisting of *E. coli* K12 BE827/pKC222, *E. coli* K12 BE827/pGD10, *E. coli* K12 BE827/pGD11, *E. coli* K12 BE827/pGD12, *E. coli* K12 BE827/pGD13, *E. coli* K12 BE827/pGD14, *E. coli* K12 BE827/pGD15, Mouse Ltk−/pGD10, Mouse Ltk−/pGD11, Mouse Ltk−/pGD12, Mouse Ltk−/pGD13, Mouse Ltk−/pGD14, and Mouse Ltk−/pGD15.

60. The transformed host cell of claim 59 which is *E. coli* K12 BE827/pKC222.

61. The transformed host cell of claim 59 which is Mouse Ltk−/pGD10.

62. The transformed host cell of claim 59 which is Mouse Ltk−/pGD13.

63. The transformed host cell of claim 59 which is Mouse Ltk−/pGD14.

64. A plasmid selected from the group consisting of plasmid pSC701, pKC257, pKC259, pKC261, pKC275, pKC264, pLO378, pKC273, pLO314, pLO315, pLO316, pLO317, pLO318, pLO319, pLO320, and pLO321.

65. The plasmid of claim 64 which is plasmid pSC701.

66. The plasmid of claim 64 which is plasmid pKC257.

67. The plasmid of claim 64 which is plasmid pKC259.

68. The plasmid of claim 64 which is plasmid pKC261.

69. The plasmid of claim 64 which is plasmid pKC275.

70. The plasmid of claim 64 which is plasmid pKC264.

71. The plasmid of claim 64 which is plasmid pKC273.

72. The plasmid of claim 64 which is plasmid pLO378.

73. The plasmid of claim 64 which is plasmid pLO314.

74. The plasmid of claim 64 which is plasmid pLO316.

75. The plasmid of claim 64 which is plasmid pLO318.

76. The plasmid of claim 64 which is plasmid pLO320.

77. A transformed host cell comprising a plasmid of claim 64.

78. The transformed host cell of claim 77 which is *E. coli* K12 BE827/pSC701.

79. The transformed host cell of claim 77 which is *E. coli* K12 BE783/pKC257.

80. The transformed host cell of claim 77 which is *E. coli* K12 BE783/pKC259.

81. The transformed host cell of claim 77 which is *E. coli* K12 BE783/pKC261.

82. The transformed host cell of claim 77 which is *E. coli* K12 BE1041/pKC275.

83. The transformed hose cell of claim 77 which is *E. coli* K12 BE783/pKC264.

84. The transformed host cell of claim 77 which is *E. coli* K12 BE783/pLO378.

85. The transformed host cell of claim 77 which is *E. coli* K12 BE783/pKC273.

86. The transformed host cell of claim 77 which is *E. coli* K12 BE783/pLO314.

87. The transformed host cell of claim 77 which is *E. coli* K12 BE783/pLO316.

88. The transformed host cell of claim 77 which is *E. coli* K12 BE783/pLO318.

89. The transformed host cell of claim 77 which is *E. coli* K12 BE1041/pLO320.

90. The transformed host cell of claim 77 which is *Saccharomyces cerevisiae*/pKC273.

91. The transformed host cell of claim 77 which is *Saccharomyces cerevisiae*/pLO378.

92. The transformed host cell of claim 77 which is Mouse Ltk−/pLO314.

93. The transformed host cell of claim 77 which is Mose Ltk−/pLO316.

94. The transformed host cell of claim 77 which is Mouse Ltk−/pLO318.

95. The transformed host cell of claim 77 which is Mouse Ltk−/pLO320.

96. The transformed host cell of claim 77 which is prokaryotic.

97. A eukaryotic host cell transformed with a vector selected from the group consisting of plasmids pLO378, pLO314, pLO315, pLO316, pLO317, pLO318, pLO319, pLO320, and pLO321.

98. A constructed hygromycin B phosphotransferaseencoding DNA sequence which comprises recombinant DNA comprising the sequence

```
         GA
         ||
         CT

GCT CAT GAG CGG AGA ACG AGA TGA CGT TGG AGG GGC AAG
||| ||| ||| ||| ||| ||| ||| ||| ||| ||| ||| ||| |||
CGA GTA CTC GCC TCT TGC TCT ACT GCA ACC TCC CCG TTC

GTC GCG CTG ATT GCT GGG GCA ACA CGT GGA GCG GAT CGG
||| ||| ||| ||| ||| ||| ||| ||| ||| ||| ||| ||| |||
CAG CGC GAC TAA CGA CCC CGT TGT GCA CCT CGC CTA GCC

GGA TTG TCT TTC TTC AGC TCG CTG ATG ATA TGC TGA CGC
||| ||| ||| ||| ||| ||| ||| ||| ||| ||| ||| ||| |||
CCT AAC AGA AAG AAG TCG AGC GAC TAC TAT ACG ACT GCG

TCA ATG CCG TTT GGC CTC CGA CTA ACG AAA ATC CCG CAT
||| ||| ||| ||| ||| ||| ||| ||| ||| ||| ||| ||| |||
AGT TAC GGC AAA CCG GAG GCT GAT TGC TTT TAG GGC GTA

TTG GAC GGC TGA TCC GAT TGG CAC GGC GGA CGG CGA ATG
||| ||| ||| ||| ||| ||| ||| ||| ||| ||| ||| ||| |||
AAC CTG CCG ACT AGG CTA ACC GTG CCG CCT GCC GCT TAC

GCG GAG CAG ACG CTC GTC CGG GGG CAA TGA GAT ATG AAA
||| ||| ||| ||| ||| ||| ||| ||| ||| ||| ||| ||| |||
CGC CTC GTC TGC GAG CAG GCC CCC GTT ACT CTA TAC TTT

AAG CCT GAA CTC ACC GCG ACG TCT GTC GAG AAG TTT CTG
||| ||| ||| ||| ||| ||| ||| ||| ||| ||| ||| ||| |||
TTC GGA CTT GAG TGG CGC TGC AGA CAG CTC TTC AAA GAC
```

```
ATC GAA AAG TTC GAC AGC GTC TCC GAC GT  ATG CAG CTC
||| ||| ||| ||| ||| ||| ||| ||| ||| ||  ||| ||| |||
TAG CTT TTC AAG CTG TCG CAG AGG CTG GAC TAC GTC GAG

TCG GAG GGC GAA GAA TCT CGT GCT TTC AGC TTC GAT GTA
||| ||| ||| ||| ||| ||| ||| ||| ||| ||| ||| ||| |||
AGC CTC CCG CTT CTT AGA GCA CGA AAG TCG AAG CTA CAT

GGA GGG CGT GGA TAT GTC CTT CGG GTA AAT AGC TGC GCC
||| ||| ||| ||| ||| ||| ||| ||| ||| ||| ||| ||| |||
CCT CCC GCA CCT ATA CAG GAC GCC CAT TTA TCG ACG CGG

GAT GGT TTC TAC AAA GAT CGT TAT GTT TAT CGG CAC TTT
||| ||| ||| ||| ||| ||| ||| ||| ||| ||| ||| ||| |||
CTA CCA AAG ATG TTT CTA GCA ATA CAA ATA GCC GTG AAA

GCA TCG GCC GCG CTC CCG ATT CCG GAA GTG CTT GAC ATT
||| ||| ||| ||| ||| ||| ||| ||| ||| ||| ||| ||| |||
CGT AGC CGG CGC GAG GGC TAA GGC CTT CAC GAA CTG TAA

GGG GAA TTC AGC GAG AGC CTG ACC TAT TGC ATC TCC CGC
||| ||| ||| ||| ||| ||| ||| ||| ||| ||| ||| ||| |||
CCC CTT AAG TCG CTC TCG GAC TGG ATA ACG TAG AGG GCG

CGT GCA CAG GGT GTC ACG TTG CAA GAC CTG CCT GAA ACC
||| ||| ||| ||| ||| ||| ||| ||| ||| ||| ||| ||| |||
GCA CGT GTC CCA CAG TGC AAC GTT CTG GAC GGA CTT TGG

GAA CTG CCC GCT GTT CTG CAG CCG GTC GCG GAG GCC ATG
||| ||| ||| ||| ||| ||| ||| ||| ||| ||| ||| ||| |||
CTT GAC GGG CGA CAA GAC GTC GGC CAG CGC CTC CGG TAC

GAT GCG ATC GCT GCG GCC GAT CTT AGC CAC ACG AGC GGG
||| ||| ||| ||| ||| ||| ||| ||| ||| ||| ||| ||| |||
CTA CGC TAG CGA CGC CGG CTA GAA TCG GTG TGC TCG CCC

TTC GGC CCA TTc GGA CCG CAA GGA ATC GGT CAA TAC ACT
||| ||| ||| ||| ||| ||| ||| ||| ||| ||| ||| ||| |||
AAG CCG GGT AAG CCT GGC GTT CCT TAG CCA GTT ATG TGA

ACA TGG CGT GAT TTC ATA TGC GCG ATT GCT GAT CCC CAT
||| ||| ||| ||| ||| ||| ||| ||| ||| ||| ||| ||| |||
TGT ACC GCA CTA AAG TAT ACG CGC TAA CGA CTA GGG GTA

GTG TAT CAC TGG CAA ACT GTG ATG GAC GAC ACC GTC AGT
||| ||| ||| ||| ||| ||| ||| ||| ||| ||| ||| ||| |||
CAC ATA GTG ACC GTT TGA CAC TAC CTG CTG TGG CAG TCA

GCG TCC GTC GCG CAG GCT CTC GAT GAG CTG ATG CTT TGG
||| ||| ||| ||| ||| ||| ||| ||| ||| ||| ||| ||| |||
CGC AGG CAG CGC GTC CGA GAG CTA CTC GAC TAC GAA ACC
```

-continued

```
GCC GAG GAC TGC CCC GAA GTC CGG CAC CTC GTG CAC GCG
 |||  |||  |||  |||  |||  |||  |||  |||  |||  |||  |||  |||  |||
CGG CTC CTG ACG GGG CTT CAG GCC GTG GAG CAC GTG CGC

GAT TTC GGC TCC AAC AAT GTC CTG ACG GAC AAT GGC CGC
 |||  |||  |||  |||  |||  |||  |||  |||  |||  |||  |||  |||  |||
CTA AAG CCG AGG TTG TTA CAG GAC TGC CTG TTA CCG GCG

ATA ACA GCG  GTC ATT  GAC TGG AGC GAG GCG ATG TTC GGG
 |||  |||  |||  ||||||   |||  |||  |||  |||  |||  |||  |||  |||
TAT TGT CGC  CAG TAA  CTG ACC TCG CTC CGC TAC AAG CCC

GAT TCC CAA TAC GAG GTC GCC AAC ATC TTC TTC TGG AGG
 |||  |||  |||  |||  |||  |||  |||  |||  |||  |||  |||  |||  |||
CTA AGG GTT ATG CTC CAG CGG TTG TAG AAG AAG ACC TCC

CCG TGG TTG GCT TGT ATG GAG CAG CAG ACG CGC TAC TTC
 |||  |||  |||  |||  |||  |||  |||  |||  |||  |||  |||  |||  |||
GGC ACC AAC CGA ACA TAC CTC GTC GTC TGC GCG ATG AAG

GAG CGG AGG CAT CC G GAG CTT GCA GGA TCG CCG CGG CTC
 |||  |||  |||  |||  ||  |  |||  |||  |||  |||  |||  |||  |||  |||
CTC GCC TCC GTA GG C CTC GAA CGT CCT AGC GGC GCC GAG

CGG GCG TAT ATG CTC CGC ATT GGT CTT GAC CAA CTC TAT
 |||  |||  |||  |||  |||  |||  |||  |||  |||  |||  |||  |||  |||
GCC CGC ATA TAC GAG GCG TAA CCA GAA CTG GTT GAG ATA

CAG AGC TTG GTT GAC GGC AAT TTC GAT GAT GCA GCT TGG
 |||  |||  |||  |||  |||  |||  |||  |||  |||  |||  |||  |||  |||
GTC TCG AAC CAA CTG CCG TTA AAG CTA CTA CGT CGA ACC

GCG CAG GGT CGA TGC GAC GCA ATC GTC CGA TCC GGA GCC
 |||  |||  |||  |||  |||  |||  |||  |||  |||  |||  |||  |||  |||
CGC GTC CCA GCT ACG CTG CGT TAG CAG GCT AGG CCT CGG

GGG ACT GTC GGG CGT ACA CAA ATC GCC CGC AGA AGC GCG
 |||  |||  |||  |||  |||  |||  |||  |||  |||  |||  |||  |||  |||
CCC TGA CAG CCC GCA TGT GTT TAG CGG GCG TCT TCG CGC

GCC GTC TGG ACC GAT GGC TGT GTA GAA GTA CTC GCC GAT
 |||  |||  |||  |||  |||  |||  |||  |||  |||  |||  |||  |||  |||
CGG CAG ACC TGG CTA CCG ACA CAT CTT CAT GAG CGG CTA

AGT GGA AAC CGA CGC CCC AGC ACT CGT CCG AGG GCA AAG
 |||  |||  |||  |||  |||  |||  |||  |||  |||  |||  |||  |||  |||
TCA CCT TTG GCT GCG GGG TCG TGA GCA GGC TCC CGT TTC

GAA TAG AGT AGA TGC CGA CCG AAC AAG AGC TGA TTT CGA
 |||  |||  |||  |||  |||  |||  |||  |||  |||  |||  |||  |||  |||
CTT ATC TCA TCT ACG GCT GGC TTG TTC TCG ACT AAA GCT
```

```
GAA CCC CTC AGC CAG CAA CTC GCG CGA GCC TAG CAA GGC
||| ||| ||| ||| ||| ||| ||| ||| ||| ||| ||| ||| |||
CTT GCG GAG TCG GTC GTT GAG CGC GCT CGG ATC GTT CCG

AAA TGC GAG AGA ACG GCC TTA CGC TTG GTG GCA CAG TTT
||| ||| ||| ||| ||| ||| ||| ||| ||| ||| ||| ||| |||
TTT ACG CTC TCT TGC CGG AAT GCG AAC CAC CGT GTC AAG

TCG TCC ACA GTT CGC TAA GCT CGC TCG GCT GGG TCG CGG
||| ||| ||| ||| ||| ||| ||| ||| ||| ||| ||| ||| |||
AGC AGG TGT CAA GCG ATT CGA GCG AGC CGA CCC AGC GCC

GAG GGC CGG TCG CAG TGA TTC AGG CCC TTC TGG ATT GTG
||| ||| ||| ||| ||| ||| ||| ||| ||| ||| ||| ||| |||
CTC CCG GCC AGC GTC ACT AAG TCC GGG AAG ACC TAA CAC

TTG GTC CCC AGG GCA CGA TTG TCA TGC CCA CGC ACT CGG
||| ||| ||| ||| ||| ||| ||| ||| ||| ||| ||| ||| |||
AAC CAG GGG TCC CGT GCT AAC AGT ACG GGT GCG TGA GCC

GTG ATC TGA CTG ATC CCG CAG ATT GGA GAT CGC CGC CCG
||| ||| ||| ||| ||| ||| ||| ||| ||| ||| ||| ||| |||
CAC TAG ACT GAC RAG GGC GTC TAA CCT CTA GCG GCG GGC

TGC CTG CCG ATT GGG TGC AGA TCT
||| ||| ||| ||| ||| ||| ||| |||
ACG GAC GGC TAA CCC ACG TCT AGA
``` wherein
A is deoxyandenyl,
G is deoxyguanidyl,
C is deoxycytisyl and
T is thymidyl.

99. A constructed hygromycin B phosphotransferaseencoding DNA sequence which comprises recombinant DNA comprising the sequence

```
ATG AAA AAG CCT GAA CTC ACC GCG ACG TCT GTC GAG AAG
||| ||| ||| ||| ||| ||| ||| ||| ||| ||| ||| ||| |||
TAC TTT TTC GGA CTT GAG TGG CGC TGC AGA CAG CTC TTC

TTT CTG ATC GAA AAG TTC GAC AGC GTC TCC GAC CTG ATG
||| ||| ||| ||| ||| ||| ||| ||| ||| ||| ||| ||| |||
AAA GAC TAG CTT TTC AAG CTG TCG CAG AGG CTG GAC TAC

CAG CTC TCG GAG GGC GAA GAA TCT CGT GCT TTT AGC TTC
||| ||| ||| ||| ||| ||| ||| ||| ||| ||| ||| ||| |||
GTC GAG AGC CTC CCG CTT CTT AGA GCA CGA AAG TCG AAG

GAT GTA GGA GGG CGT GAA TAT GTC CTG CGG GTA AAT AGC
||| ||| ||| ||| ||| ||| ||| ||| ||| ||| ||| ||| |||
CTA CAT CCT CCC GCA CTT ATA CAG GAC GCC CAT TTA TCG

TGC GCC GAT GGT TTC TAC AAA GAT CGT TAT GTT TAT CGG
||| ||| ||| ||| ||| ||| ||| ||| ||| ||| ||| ||| |||
ACG CGG CTA CCA AAG ATG TTT CTA GCA ATA CAA ATA GCC
```

-continued

```
CAC TTT GCA TCG GCC GCG CTC CCG ATT CCG GAA GTG CTT
 |   |   |   |   |   |   |   |   |   |   |   |
GTG AAA CGT AGC CGG CGC GAG GGC TAA GGC CTT CAC GAA

GAC ATT GGG GAA TTC AGC GAG AGC CTG ACC TAT TGC ATC
 |   |   |   |   |   |   |   |   |   |   |   |   |
CTG TAA CCC CTT AAG TCG CTC TCG GAC TGG ATA ACG TAG

TCC CGC CGT GCA CAG GGT GTC ACG TTG CAA GAC CTG CCT
 |   |   |   |   |   |   |   |   |   |   |   |   |
AGG GCG GCA CGT GTC CCA CAG TGC AAC GTT CTG GAC GGA

GAA ACC GAA CTG CCC GCT GTT CTG CAG CGG GTC GCG GAG
 |   |   |   |   |   |   |   |   |   |   |   |   |
CTT TGG CTT GAC GGG CGA CAA GAC GTC GCC CAG CGC CTC

GCC ATG GAT GCG ATC GCT GCG GCC GAT CTT AGC CAG ACG
 |   |   |   |   |   |   |   |   |   |   |   |   |
CGG TAC CTA CGC TAG CGA CGC CGG CTA GAA TCG GTC TGC

AGC CCC TTC GGC CCA TTC GGA CCG CAA GGA ATC GGT CAA
 |   |   |   |   |   |   |   |   |   |   |   |   |
TTG GGG AAG CCG GGT AAG CCT GGC GTT CCT TAG CCA GTT

TAC ACT ACA TGG CGT GAT TTC ATA TGC GCG ATT GCT GAT
 |   |   |   |   |   |   |   |   |   |   |   |   |
ATG TGA TGT ACC GCA CTA AAG TAT ACG CGC TAA CGA CTA

CCC CAT GTG TAT CAC TGC CAA ACT GTG ATG GAC GAC ACC
 |   |   |   |   |   |   |   |   |   |   |   |   |
GGG GTA CAC ATA GTG ACG GTT TGA CAC TAC CTG CTG TGG

GTC AGT GCG TCC GTC GCG CAG GCT CTC GAT GAG CTG ATG
 |   |   |   |   |   |   |   |   |   |   |   |   |
CAG TCA CGC AGG CAG CGC GTC CGA GAG CTA CTC GAC TAC

CTT TGG GCC GAG GAC TGC CCC GAA GTC CGG CAC CTC GTG
 |   |   |   |   |   |   |   |   |   |   |   |   |
GAA ACC CGG CTC CTG ACG GGG CTT CAG GCC GTG GAG CAC

CAC GCG GAT TTC GGC TCC AAC AAT GTC CTG ACG GAC AAT
 |   |   |   |   |   |   |   |   |   |   |   |   |
GTG CGC CTA AAG CCG AGG TTG TTA CAG GAC TGC CTG TTA

GGC CGC ATA ACA GCG GTC ATT GAC TGG AGC GAG GCG ATG
 |   |   |   |   |   |   |   |   |   |   |   |   |
CCG GCG TAT TGT CGC CAG TAA CTG ACC TCG CTC CGC TAC

TTC GGG GAT TCC CAA TAC GAG GTC GCC AAC ATC TTC TTC
 |   |   |   |   |   |   |   |   |   |   |   |   |
AAG CCC CTA AGG GTT ATG CTC CAG CGG TTG TAG AAG AAG
```

```
TGG AGG CCG TGG TTG GCT TGT ATG GAG CAG CAG ACG CGC
||| ||| ||| ||| ||| ||| ||| ||| ||| ||| ||| ||| |||
ACC TCC GGC ACC AAC CGA ACA TAC CTC GTC GTC TGC GCG

TAC TTC GAG CGG AGG CAT CCG GAG CTT GCA GGA TCG CCG
||| ||| ||| ||| ||| ||| ||| ||| ||| ||| ||| ||| |||
ATG AAG CTC GCC TCC GTA GGC CTC GAA CGT CCT AGC GGC

CGG CTC CGG GCG TAT ATG CTC CGC ATT GGT CTT GAC CAA
||| ||| ||| ||| ||| ||| ||| ||| ||| ||| ||| ||| |||
GCC GAG GCC CGC ATA TAC GAG GCG TAA CCA GAA CTG GTT

GCT TGG GCG CAG GGT CGA TGC GAC GCA ATC GTC CGA TCC
||| ||| ||| ||| ||| ||| ||| ||| ||| ||| ||| ||| |||
CGA ACC CGC GTC CCA GCT ACG CTG CGT TAG CAG GCT AGG

GGA GCC GGG ACT GTC GGG CGT ACA CAA ATC GCC CGC AGA
||| ||| ||| ||| ||| ||| ||| ||| ||| ||| ||| ||| |||
CCT CGG CCC TGA CAG CCC GCA TGT GTT TAG CGG GCG TCT

AGC GCG GCC GTC TGG ACC GAT GGC TGT GTA GAA GTA CTC
||| ||| ||| ||| ||| ||| ||| ||| ||| ||| ||| ||| |||
TCG CGC CGG CAG ACC TGG CTA CCG ACA CAT CTT CAT GAG

GCC GAT AGT GGA AAC CGA CGC CCC AGC ACT CGT CCG AGG
||| ||| ||| ||| ||| ||| ||| ||| ||| ||| ||| ||| |||
CGG CTA TCA CCT TTG GCT GCG GGG TCG TGA GCA GGC TCC

GCA AAG GAA TAG
||| ||| ||| |||
CGT TTC CTT ATC
``` wherein
A is deoxyadenyl,
G is deoxyguanidyl,
C is deoxycytisyl and
T is thymidyl.

100. A constructed DNA sequence that comprises recombinant DNA that encodes a polypeptide comprising the amino acid sequence

| MET | LYS | LYS | PRO | GLU | LEU | THR | ALA | THR | SER | VAL | GLU | LYS |
|-----|-----|-----|-----|-----|-----|-----|-----|-----|-----|-----|-----|-----|
| PHE | LEU | ILE | GLU | LYS | PHE | ASP | SER | VAL | SER | ASP | LEU | MET |
| GLN | LEU | SER | GLU | GLY | GLU | GLU | SER | ARG | ALA | PHE | SER | PHE |
| ASP | VAL | GLY | GLY | ARG | GLY | TYR | VAL | LEU | ARG | VAL | ASN | SER |
| CYS | AKA | ASP | GLY | PHE | TYR | LYS | ASP | ARG | TYR | VAL | TYR | ARG |
| HIS | PHE | ALA | SER | ALA | ALA | LEU | PRO | ILE | PRO | GLU | VAL | LEU |
| ASP | ILE | GLY | GLU | PHE | SER | GLU | SER | LEU | THR | TYR | CYS | ILE |
| SER | ARG | ARG | ALA | GLN | GLY | VAL | THR | LEU | GLN | ASP | LEU | PRO |
| GLU | THR | GLU | LEU | PRO | ALA | VAL | LEU | GLN | PRO | VAL | ALA | GLU |
| ALA | MET | ASP | ALA | ILE | ALA | ALA | ALA | ASP | LEU | SER | GLN | THR |
| SER | GLY | PHE | GLY | PRO | PHE | GLY | PRO | GLN | GLY | ILE | GLY | GLN |
| TYR | THR | THR | TRP | ARG | ASP | PHE | ILE | CYS | ALA | ILE | ALA | ASP |
| PRO | HIS | VAL | TYR | HIS | TRP | GLN | THR | VAL | MET | ASP | ASP | THR |
| VAL | SER | ALA | SER | VAL | ALA | GLN | ALA | LEU | ASP | GLU | LEU | MET |
| LEU | TRP | ALA | GLU | ASP | CYS | PRO | GLU | VAL | ARG | HIS | LEU | VAL |
| HIS | ALA | ASP | PHE | GLY | SER | ASN | ASN | VAL | LEU | THR | ASP | ASN |
| GLY | ARG | ILE | THR | ALA | VAL | ILE | ASP | TRP | SER | GLU | ALA | MET |
| PHE | GLY | ASP | SER | GLN | TYR | GLU | VAL | ALA | ASN | ILE | PHE | PHE |
| TRP | ARG | PRO | TRP | LEU | ALA | CYS | MET | GLU | GLN | GLN | THR | ARG |
| TYR | PHE | GLU | ARG | ARG | HIS | PRO | GLU | LEU | ALA | GLY | SER | PRO |
| ARG | LEU | ARG | ALA | TYR | MET | LEU | ARG | ILE | GLY | LEU | ASP | GLN |
| LEU | TYR | GLN | SER | LEU | VAL | ASP | GLY | ASN | PHE | ASP | ASP | ALA |
| ALA | TRP | ALA | GLN | GLY | ARG | CYS | ASP | ALA | ILE | VAL | ARG | SER |
| GLY | ALA | GLY | THR | VAL | GLY | ARG | THR | GLN | ILE | ALA | ARG | ARG |
| SER | ALA | ALA | VAL | TRP | THR | ASP | GLY | CYS | VAL | GLU | VAL | LEU |
| ALA | ASP | SER | GLY | ASN | ARG | ARG | PRO | SER | THR | ARG | PRO | ARG |

| ALA | LYS | GLU | wherein
- MET is methionine,
- LYS is lysine,
- PRO is proline,
- GLU is glutamic acid,
- LEU is leucine,
- THR is threonine,
- ALA is alanine,
- SER is serine,
- VAL is valine,
- PHE is phenylalanine,
- ILE is isoleucine,
- GLY is glycine,
- ASP is aspartic acid,
- GLN is glutamine,
- ARG is arginine,
- CYS is cysteine,
- TRP is tryptophan,
- ASN is asparagine,
- HIS is histidine and
- TYR is tryrosine.

101. A recombinant DNA cloning vector comprising the DNA sequence of claim 98.

102. A recombinant DNA cloning vector comprising the DNA sequence of claim 99.

103. A recombinant DNA cloning vector comprising the DNA sequence of claim 100.

104. The plasmid of claim 16 wherein the gene and associated control element comprises the DNA sequence

```
ATG AAA AAG CCT GAA CTC ACC GCG ACG TCT GTC GAG AAG
TAC TTT TTC GGA CTT GAG TGG CGC TGC AGA CAG CTC TTC

TTT CTG ATC GAA AAG TTC GAC AGC GTC TCC GAC CTG ATG
AAA GAC TAG CTT TTC AAG CTG TCG CAG AGG CTG GAC TAC

CAG CTC TCG GAG GGC GAA GAA TCT CGT GCT TTT AGC TTC
GTC GAG AGC CTC CCG CTT CTT AGA GCA CGA AAG TCG AAG

GAT GTA GGA GGG CGT GAA TAT GTC CTG CGG GTA AAT AGC
CTA CAT CCT CCC GCA CTT ATA CAG GAC GCC CAT TTA TCG

TGC GCC GAT GGT TTC TAC AAA GAT CGT TAT GTT TAT CGG
ACG CGG CTA CCA AAG ATG TTT CTA GCA ATA CAA ATA GCC

CAC TTT GCA TCG GCC GCG CTC CCG ATT CCG GAA GTG CTT
GTG AAA CGT AGC CGG CGC GAG GGC TAA GGC CTT CAC GAA

GAC ATT GGG GAA TTC AGC GAG AGC CTG ACC TAT TGC ATC
CTG TAA CCC CTT AAG TCG CTC TCG GAC TGG ATA ACG TAG

TCC CGC CGT GCA CAG GGT GTC ACG TTG CAA GAC CTG CCT
AGG GCG GCA CGT GTC CCA CAG TGC AAC GTT CTG GAC GGA

GAA ACC GAA CTG CCC GCT GTT CTG CAG CGG GTC GCG GAG
CTT TGG CTT GAC GGG CGA CAA GAC GTC GGC CAG CGC CTC
```

-continued

```
GCC ATG GAT GCG ATC GCT GCG GCC GAT CTT AGC CAG ACG
||| ||| ||| ||| ||| ||| ||| ||| ||| ||| ||| ||| |||
CGG TAC CTA CGC TAG CGA CGC CGG CTA GAA TCG GTC TGC

AGC CCC TTC GGC CCA TTC GGA CCG CAA GGA ATC GGT CAA
||| ||| ||| ||| ||| ||| ||| ||| ||| ||| ||| ||| |||
TTG GGG AAG CCG GGT AAG CCT GGC GTT CCT TAG CCA GTT

TAC ACT ACA TGG CGT GAT TTC ATA TGC GCG ATT GCT GAT
||| ||| ||| ||| ||| ||| ||| ||| ||| ||| ||| ||| |||
ATG TGA TGT ACC GCA CTA AAG TAT ACG CGC TAA CGA CTA

CCC CAT GTG TAT CAC TGC CAA ACT GTG ATG GAC GAC ACC
||| ||| ||| ||| ||| ||| ||| ||| ||| ||| ||| ||| |||
GGG GTA CAC ATA GTG ACC GTT TGA CAC TAC CTG CTG TGG

GTC AGT GCG TCC GTC GCG CAG GCT CTC GAT GAG CTG ATG
||| ||| ||| ||| ||| ||| ||| ||| ||| ||| ||| ||| |||
CAG TCA CGC AGG CAG CGC GTC CGA GAG CTA CTC GAC TAC

CTT TGG GCC GAG GAC TGC CCC GAA GTC CGG CAC CTC GTG
||| ||| ||| ||| ||| ||| ||| ||| ||| ||| ||| ||| |||
GAA ACC CGG CTC CTG ACG GGG CTT CAG GCC GTG GAG CAC

CAC GCG GAT TTC GGC TCC AAC AAT GTC CTG ACG GAC AAT
||| ||| ||| ||| ||| ||| ||| ||| ||| ||| ||| ||| |||
GTG CGC CTA AAG CCG AGG TTG TTA CAG GAC TGC CTG TTA

GGC CGC ATA ACA GCG GTC ATT GAC TGG AGC GAG GCG ATG
||| ||| ||| ||| ||| ||| ||| ||| ||| ||| ||| ||| |||
CCG GCG TAT TGT CGC CAG TAA CTG ACC TCG CTC CGC TAC

TTC GGG GAT TCC CAA TAC GAG GTC GCC AAC ATC TTC TTC
||| ||| ||| ||| ||| ||| ||| ||| ||| ||| ||| ||| |||
AAG CCC CTA AGG GTT ATG CTC CAG CGG TTG TAG AAG AAG

TGG AGG CCG TGG TTG GCT TGT ATG GAG CAG CAG ACG CGC
||| ||| ||| ||| ||| ||| ||| ||| ||| ||| ||| ||| |||
ACC TCC GGC ACC AAC CGA ACA TAC CTC GTC GTC TGC GCG

TAC TTC GAG CGG AGG CAT CCG GAG CTT GCA GGA TCG CCG
||| ||| ||| ||| ||| ||| ||| ||| ||| ||| ||| ||| |||
ATG AAG CTC GCC TCC GTA GGC CTC GAA CGT CCT AGC GGC

CGG CTC CGG GCG TAT ATG CTC CGC ATT GGT CTT GAC CAA
||| ||| ||| ||| ||| ||| ||| ||| ||| ||| ||| ||| |||
GCC GAG GCC CGC ATA TAC GAG GCG TAA CCA GAA CTG GTT

GCT TGG GCG CAG GGT CGA TGC GAC GCA ATC GTC CGA TCC
||| ||| ||| ||| ||| ||| ||| ||| ||| ||| ||| ||| |||
CGA ACC CGC GTC CCA GCT ACG CTG CGT TAG CAG GCT AGG
```

```
                                              -continued
GGA  GCC  GGG  ACT  GTC  GGG  CGT  ACA  CAA  ATC  GCC  CGC  AGA
|||  |||  |||  |||  |||  |||  |||  |||  |||  |||  |||  |||  |||
CCT  CGG  CCC  TGA  CAG  CCC  GCA  TGT  GTT  TAG  CGG  GCG  TCT

GCA  AAG  GAA  TAG
|||  |||  |||  |||
CGT  TTC  CTT  ATC
``` wherein
- A is deoxyadenyl,
- G is deoxyguanidyl, C is deoxycytisyl and
- T is thymidyl.

105. The plasmid of claim 16 wherein the gene and associated control element encodes a hygromycin B resistance-conferring polypeptide comprising the amino acid sequence

- ASP is aspartic acid,
- GLN is glutamine,
- ARG is arginine,
- CYS is cysteine,
- TRP is tryptophan,
- ASN is asparagine,
- HIS is histidine and
- TYR is tyrosine.

| MET | LYS | LYS | PRO | GLU | LEU | THR | ALA | THR | SER | VAL | GLU | LYS |
|-----|-----|-----|-----|-----|-----|-----|-----|-----|-----|-----|-----|-----|
| PHE | LEU | ILE | GLU | LYS | PHE | ASP | SER | VAL | SER | ASP | LEU | MET |
| GLN | LEU | SER | GLU | GLY | GLU | GLU | SER | ARG | ALA | PHE | SER | PHE |
| ASP | VAL | GLY | GLY | ARG | GLY | TYR | VAL | LEU | ARG | VAL | ASN | SER |
| CYS | AKA | ASP | GLY | PHE | TYR | LYS | ASP | ARG | TYR | VAL | TYR | ARG |
| HIS | PHE | ALA | SER | ALA | ALA | LEU | PRO | ILE | PRO | GLU | VAL | LEU |
| ASP | ILE | GLY | GLU | PHE | SER | GLU | SER | LEU | THR | TYR | CYS | ILE |
| SER | ARG | ARG | ALA | GLN | GLY | VAL | THR | LEU | GLN | ASP | LEU | PRO |
| GLU | THR | GLU | LEU | PRO | ALA | VAL | LEU | GLN | PRO | VAL | ALA | GLU |
| ALA | MET | ASP | ALA | ILE | ALA | ALA | ALA | ASP | LEU | SER | GLN | THR |
| SER | GLY | PHE | GLY | PRO | PHE | GLY | PRO | GLN | GLY | ILE | GLY | GLN |
| TYR | THR | THR | TRP | ARG | ASP | PHE | ILE | CYS | ALA | ILE | ALA | ASP |
| PRO | HIS | VAL | TYR | HIS | TRP | GLN | THR | VAL | MET | ASP | ASP | THR |
| VAL | SER | ALA | SER | VAL | ALA | GLN | ALA | LEU | ASP | GLU | LEU | MET |
| LEU | TRP | ALA | GLU | ASP | CYS | PRO | GLU | VAL | ARG | HIS | LEU | VAL |
| HIS | ALA | ASP | PHE | GLY | SER | ASN | ASN | VAL | LEU | THR | ASP | ASN |
| GLY | ARG | ILE | THR | ALA | VAL | ILE | ASP | TRP | SER | GLU | ALA | MET |
| PHE | GLY | ASP | SER | GLN | TYR | GLU | VAL | ALA | ASN | ILE | PHE | PHE |
| TRP | ARG | PRO | TRP | LEU | ALA | CYS | MET | GLU | GLN | GLN | THR | ARG |
| TYR | PHE | GLU | ARG | ARG | HIS | PRO | GLU | LEU | ALA | GLY | SER | PRO |
| ARG | LEU | ARG | ALA | TYR | MET | LEU | ARG | ILE | GLY | LEU | ASP | GLN |
| LEU | TYR | GLN | SER | LEU | VAL | ASP | GLY | ASN | PHE | ASP | ASP | ALA |
| ALA | TRP | ALA | GLN | GLY | ARG | CYS | ASP | ALA | ILE | VAL | ARG | SER |
| GLY | ALA | GLY | THR | VAL | GLY | ARG | THR | GLN | ILE | ALA | ARG | ARG |
| SER | ALA | ALA | VAL | TRP | THR | ASP | GLY | CYS | VAL | GLU | VAL | LEU |
| ALA | ASP | SER | GLY | ASN | ARG | ARG | PRO | SER | THR | ARG | PRO | ARG |
| ALA | LYS | GLU |     |     |     |     |     |     |     |     |     |     | wherein
- MET is methionine,
- LYS is lysine,
- PRO is proline,
- GLU is glutamic acid,
- LEU is leucine,
- THR is threonine,
- ALA is alanine,
- SER is serine,
- VAL is valine,
- PHE is phenylalanine,
- ILE is isoleucine,
- GLY is glycine, 106. A transformed host cell comprising the recombinant DNA cloning vector of claim 102.

107. A transformed host cell comprising the recombinant DNA cloning vector of claim 103.

108. The transformed host cell of claim 106 which is *E. coli*.

109. The transformed host cell of claim 107 which is *Saccharomyces cerevisiae*.

110. A transformed host cell comprising the plasmid of claim 104.

111. A transformed host cell comprising the plasmid of claim 105.

* * * * *

UNITED STATES PATENT AND TRADEMARK OFFICE
CERTIFICATE OF CORRECTION

PATENT NO. : 4,727,028                     Page 1 of 5

DATED     : 2/23/88

INVENTOR(S) : Santerre, et al.

It is certified that error appears in the above-identified patent and that said Letters Patent is hereby corrected as shown below:

In column 33, line 35, "BglII" should read -- BglII --.

In column 33, line 41, "BglII" should read -- BglII --.

In column 33, line 44, "BglII" should read -- BglII --.

In column 34, line 5, "adenvirus" should read -- adenovirus --.

In column 34, line 37, "BglII/SalI" should read -- BglII/SalI --.

In column 34, line 45, "C" should read -- B --.

In column 34, line 45, "SacI/BglII" should read -- SacI/BglII --.

In column 34, line 49, "EcoRI/SalI" should read -- EcoRI/SalI --.

In column 35, line 9, "BglII" should read -- BglII --.

In column 35, line 10, "BglII/SalI" should read -- BglII/SalI --.

In column 35, line 11, "1.5 kb SacI/BglII" should read -- 1.5 kb SacI/BglI --.

In column 35, line 12, "Eco-" should read -- Eco- --.

In column 35, line 13, "SalI" should read -- SalI --.

In column 35, line 15, "BglII" should read -- BglII --.

In column 35, line 17, "BglII/SalI" should read -- BglII/SalI --.

In column 35, line 20, "151 kb SacI/BglII" should read -- 1.51 kb SacI/BglII --.

In column 35, line 23, "EcoRI/SalI" should read -- EcoRI/SalI --.

UNITED STATES PATENT AND TRADEMARK OFFICE
CERTIFICATE OF CORRECTION

PATENT NO. : 4,727,028

DATED : 2/23/88

INVENTOR(S) : Santerre, et al.

It is certified that error appears in the above-identified patent and that said Letters Patent is hereby corrected as shown below:

In column 35, line 47, "Bacillus" should read -- *Bacillus* --.

In column 35, line 48, "Streptomyces" should read -- *Streptomyces* --.

In column 35, line 54, "Streptomyces" should read -- *Streptomyces* --.

In column 35, line 58, "Neurospora" should read -- *Neurospora* --.

In column 35, line 59, "Cephalosporium, Aspergillus, Penicillium" should read -- *Cephalosporium, Aspergillus, Penicillium* --.

In column 35, line 61, "Neurospora" should read -- *Neurospora* --.

In column 35, line 63, "Cephalosporium" should read -- *Cephalosporium* --.

In column 37, line 19, "hose" should read -- host --.

In column 38, line 14, "Mose" should read -- Mouse --.

In column 39, the first line of DNA sequence, "GT " should read -- CTG --.
'  '                                                                '''
GAC                                                                 GAC In column 39, the third line of DNA sequence, "CTT" should read -- CTG --.
'''                                                                 '''
GAC                                                                 GAC In column 39, the tenth line of DNA sequence, "TTc" should read -- TTC --.
'''                                                                 '''
AAG                                                                 AAG

UNITED STATES PATENT AND TRADEMARK OFFICE
CERTIFICATE OF CORRECTION

PATENT NO. : 4,727,028            Page 3 of 5

DATED : 2/23/88

INVENTOR(S) : Santerre, et al.

It is certified that error appears in the above-identified patent and that said Letters Patent is hereby corrected as shown below:

In column 43, the first line of DNA sequence, "CCC" should read -- CGC --.
                                                                          '''              '''
                                                                          GCG            GCG In column 43, the second line of DNA sequence, "TTT" should read -- TTC --.
                                                                        '''            '''
                                                                       AAG          AAG In column 43, the sixth line of DNA sequence, "ATC" should read -- ATC --.
                                                                    '''             '''
                                                                  RAG           TAG In column 43, line 38, "A is deoxyandenyl," should read -- A is deoxyadenyl, --.

In column 44, the third line of DNA sequence, "TTT" should read -- TTC --.
                                                            '''             '''
                                                           AAG           AAG In column 44, the fourth line of DNA sequence, "GAA" should read -- GGA --.
                                                         '''             '''
                                                         CTT            CCT In column 45, the fourth line of DNA sequence, "CGG" should read -- CCG --.
                                                        '''             '''
                                                         GGC            GGC In column 45, the sixth line of DNA sequence, "AGC CCC" should read
                                                           ''' '''
-- AGC GGG --.                       TTG GGG
   ''' '''
   TCG CCC

UNITED STATES PATENT AND TRADEMARK OFFICE
CERTIFICATE OF CORRECTION

PATENT NO. : 4,727,028                   Page 4 of 5

DATED : 2/23/88

INVENTOR(S) : Santerre, et al.

It is certified that error appears in the above—identified patent and that said Letters Patent is hereby corrected as shown below:

In column 45, the eighth line of DNA sequence, "TGC" should read -- TGG --.
```
                                                 ''' '''         ''' '''
                                                 ACC             ACC
```

In column 47, between the third and fourth lines of DNA sequence, insert the line of DNA sequence, -- CTC TAT CAG AGC TTG GTT GAC GGC AAT TTC GAT GAT GCA --.
```
   ''' ''' ''' ''' ''' ''' ''' ''' ''' ''' ''' ''' '''
   GAG ATA GTC TCG AAC CAA CTG CCG TTA AAG CTA CTA CGT
```

In column 50, line 10, "TYR is tryrosine" should read -- TYR is tyrosine --.

In column 50, the third line of DNA sequence, "TTT" should read -- TTC --.
```
                                                 '''             '''
                                                 AAG             AAG
```

In column 50, the fourth line of DNA sequence, "GAA" should read -- GGA --.
```
                                                 '''             '''
                                                 CTT             CCT
```

In column 50, the ninth line of DNA sequence, "CGG" should read -- CCG --.
```
                                                 '''             '''
                                                 GGC             GGC
```

In column 51, the second line of DNA sequence, "AGC CCC" should read
```
                                                 ''' '''
                                                 TTG GGG
```
-- AGC GGG --.
```
   ''' '''
   TCG CCC
```

UNITED STATES PATENT AND TRADEMARK OFFICE
CERTIFICATE OF CORRECTION

PATENT NO. : 4,727,028

DATED : 2/23/88

INVENTOR(S) : Santerre, et al.

It is certified that error appears in the above—identified patent and that said Letters Patent is hereby corrected as shown below:

In column 51, between the twelfth and thirteenth lines of DNA sequence, insert the line of DNA sequence,

```
-- CTC TAT CAG AGC TTG GTT GAC GGC AAT TTC GAT GAT GCA --.
   ''' ''' ''' ''' ''' ''' ''' ''' ''' ''' ''' ''' '''
   GAG ATA GTC TCG AAC CAA CTG CCG TTA AAG CTA CTA CGT
```

In column 53, between the first and second lines of DNA sequence, insert the lines of DNA sequence

```
-- AGC GCG GCC GTC TGG ACC GAT GGC TGT GTA GAA GTA CTC
   ''' ''' ''' ''' ''' ''' ''' ''' ''' ''' ''' ''' '''
   TCG CGC CGG CAG ACC TGG CTA CCG ACA CAT CTT CAT GAG

GCC GAT AGT GGA AAC CGA CGC CCC AGC ACT CGT CCG AGG --.
   ''' ''' ''' ''' ''' ''' ''' ''' ''' ''' ''' ''' '''
   CGG CTA TCA CCT TTG GCT GCG GGG TCG TGA GCA GGC TCC
```

In column 53, line 24, "AKA" should read -- ALA --.

Signed and Sealed this

Tenth Day of April, 1990

Attest:

HARRY F. MANBECK, JR.

*Attesting Officer*      *Commissioner of Patents and Trademarks*